United States Patent
Zacks

(10) Patent No.: US 8,796,223 B2
(45) Date of Patent: *Aug. 5, 2014

(54) METHODS OF INHIBITING PHOTORECEPTOR APOPTOSIS

(71) Applicant: David Noam Zacks, Ann Arbor, MI (US)

(72) Inventor: David Noam Zacks, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/691,074

(22) Filed: Jan. 8, 2013

(65) Prior Publication Data

US 2013/0123191 A1   May 16, 2013

Related U.S. Application Data

(63) Continuation of application No. 12/716,986, filed on Mar. 3, 2010, now Pat. No. 8,343,931.

(60) Provisional application No. 61/157,079, filed on Mar. 3, 2009, provisional application No. 61/254,082, filed on Oct. 22, 2009.

(51) Int. Cl.
*A61P 27/02* (2006.01)
*A61K 38/10* (2006.01)
*C07K 7/08* (2006.01)
*C07K 14/82* (2006.01)

(52) U.S. Cl.
USPC ................. 514/20.8; 530/327; 514/18.9

(58) Field of Classification Search
None
See application file for complete search history.

(56) References Cited

U.S. PATENT DOCUMENTS

| 7,811,832 B2 | 10/2010 | Zacks et al. | |
| 8,343,931 B2* | 1/2013 | Zacks | 514/20.8 |
| 2005/0129684 A1 | 6/2005 | Zacks et al. | |
| 2006/0269520 A1 | 11/2006 | Korneluk et al. | |

FOREIGN PATENT DOCUMENTS

| WO | 2005117940 A2 | 12/2005 |
| WO | WO 2007035474 A2 * | 3/2007 |
| WO | WO2009/039388 | 3/2009 |

OTHER PUBLICATIONS

Bork "Powers and Pitfalls in Sequence Analysis: The 70% Hurdle"(2000) Genome Research, vol. 10, pp. 398-400.
Besirli, et al. "Inhibition of Retinal Detachment-Induced Apoptosis in Photoreceptors by a Small Peptide Inhibitor of the Fas Receptor" 2010, Investigative Ophthalmology & Visual Science, vol. 51 (4), pp. 2177-2184.
Brenner "Error in genome annotation" (1999) Trends in Genetics, vol. 15(4), pp. 132-133.
Doerks, et al. "Protein annotation: detective work for function prediction" (1998) Trends in Genetics, vol. 14(6), pp. 248-250.
Ngo, et al. (1994) "The Protein Folding Problem and Tertiary Structure Prediction—Chapter 14: Computational Complexity Protein Structure Prediction, and the Levinthal Paradox" pp. 433-440 & 492-495.
Phillips "The challenge of gene therapy and DNA delivery" J Pharm Pharmacology, vol. 53, pp. 1169-1174 (2001).
Pirollo, et al. "Targeted Delivery of Small Interfering RNA: Approaching Effective Cancer Therapies" 2008. Cancer Res. vol. 68(5), pp. 1247-1250.
Skolnick, et al. "From genes to protein structure and function: novel applications of computational approaches in the genomic era" (2000) Trends in Biotech., vol. 18(1), pp. 34-39.
Vidal, et al. "Making sense onf antisense" 2005, European Journal of Cancer, vol. 41, pp. 2812-2818.
Wells "Additivity of Mutational Effects in Proteins" (1990) Biochemistry, vol. 29(37), pp. 8509-8517.
Cook et al., "Apoptotic photoreceptor degeneration in experimental retinal detachment," Invest Ophthalmol Vis Sci. 1995;36(6):990-996.
Hisatomi et al., "Critical role of photoreceptor apoptosis in functional damage after retinal detachment ," Curr Eye Res. 2002;24(3):161-172.
Zacks et al., "Caspase activation in an experimental model of retinal detachment ," Invest Ophthalmol Vis Sci. 2003;44(3):1262-1267.
Yang et al., "Preventing retinal detachment-associated photoreceptor cell loss in Bax-deficient mice," Invest Ophthalmol Vis Sci. 2004;45(2):648-654.
Burton, "Recovery of visual acuity after retinal detachment involving the macula," Trans Am Ophthalmol Soc. 1982; 80:475-497.
Ross et al., "Visual recovery in macula-off rhegmatogenous retinal detachments," Ophthalmology. 1998;105 (11):2149-2153.
Hassan et al., "The effect of duration of macular detachment on results after the scleral buckle repair of primary, macula-off retinal detachments," Ophthalmology. 2002;109(1):146-152.
Kanan et al., "Light induces programmed cell death by activating multiple independent proteases in a cone photoreceptor cell line," Invest Ophthalmol Vis Sci. 2007; 48(1):40-51.
Bakunowicz-Lazarczyk et al., "Comparative studies of morphological changes and interleukin concentration in subretinal fluid of patients with retinal detachment," Ophthalmologica. 1999;213(1):25-29.
Heinrich et al., "Membrane-bound and soluble interleukin-6 receptor: studies on structure, regulation of expression, and signal transduction," Ann N Y Acad Sci. 1995;762:222-236.
Inomata et al., "Neuroprotective effects of interleukin-6 on NMDA-induced rat retinal damage," Biochem Biophys Res Commun. 2003;302(2):226-232.

(Continued)

*Primary Examiner* — Zachary Howard
(74) *Attorney, Agent, or Firm* — David W. Staple; Casimir Jones, S.C.

(57) ABSTRACT

The present invention provides methods to prevent photoreceptor death. In particular, the present invention provides peptides which prevent FAS-mediated photoreceptor apoptosis.

7 Claims, 22 Drawing Sheets

(56) References Cited

OTHER PUBLICATIONS

Curnow et al., "Inhibition of T cell apoptosis in the aqueous humor of patients with uveitis by IL-6/soluble IL-6 receptor trans-signaling," J Immunol. 2004;173(8):5290-5297.
Samardzija et al., "Differential role of Jak-STAT signaling in retinal degenerations," FASEB J. 2006;20 (13):2411-2413.
Aaronson et al., "A road map for those who don't know JAK-STAT," Science. 2002;296(5573):1653-1655.
Stephanou et al., "STAT-1: a novel regulator of apoptosis," Int J Exp Pathol. 2003;84(6):239-244.
Stephanou et al., "Opposing actions of STAT-1 and STAT-3," Growth Factors. 2005;23(3):177-182.
Battle et al., "The role of STATs in apoptosis," Curr Mol Med. 2002; 2(4):381-392.
Haga et al., "Stat3 protects against Fas-induced liver injury by redox-dependent and -independent mechanisms," J Clin Invest. 2003; 112(7):989-998.
Budd et al., "cFLIP regulation of lymphocyte activation and development," Nat Rev Immunol. 2006; 6(3):196-204.
Kovalovich et al., "Interleukin-6 protects against Fas-mediated death by establishing a critical level of anti-apoptotic hepatic proteins FLIP, Bcl-2, and Bcl-xL," J Biol Chem. 2001;276(28):26605-26613.
Sanchez et al., "Interleukin-6 in retinal ischemia reperfusion injury in rats," Invest Ophthalmol Vis Sci. 2003;44 (9):4006-4011.
Tan et al., "Expression of cone-photoreceptor-specific antigens in a cell line derived from retinal tumors in transgenic mice," Invest Ophthalmol Vis Sci. 2004; 45(3):764-768.
Sappington et al., "Interleukin-6 protects retinal ganglion cells from pressure-induced death," Invest Ophthalmol Vis Sci. 2006; 47(7):2932-2942.
Hofer-Warbinek et al., "Activation of NF-kappa B by XIAP, the X chromosome-linked inhibitor of apoptosis, in endothelial cells involves TAK1," J Biol Chem 2000; 275:22064-22068.
Sanna et al., "IAP suppression of apoptosis involves distinct mechanisms: the TAK1/JNK1 signaling cascade and caspase inhibition," Mol Cell Biol 2002; 22:1754-1766.
Zacks et al., "Role of the Fas-signaling pathway in photoreceptor neuroprotection," Arch Ophthalmol 2007; 125:1389-1395.
Zacks et al., "FAS-mediated apoptosis and its relation to intrinsic pathway activation in an experimental model of retinal detachment," IOVS 2004; 45(12):4563-4569.
Chong et al., "Interleukin-6 as a photoreceptor neuroprotectant in an experimental model of retinal detachment," Invest Ophthalmol Vis Sci. 2008; 49(7):3193-3200.
Zadro-Lamoureux et al., "XIAP effects on retinal detachment-induced photoreceptor apoptosis [corrected]" Invest Ophthalmol Vis Sci. 2009; 50(3):1448-1453.
Hisatomi et al., "Relocalization of apoptosis-inducing factor in photoreceptor apoptosis induced by retinal detachment in vivo," Am J Pathol. Apr. 2001; 158(4):1271-1278.
Hisatomi et al., "HIV protease inhibitors provide neuroprotection through inhibition of mitochondrial apoptosis in mice," 2008 J Clin Invest 118: 2025-2038.
Dunaief et al., "The role of apoptosis in age-related macular degeneration," Arch Ophthalmol. 2002; 120 (11):1435-1442.
Jager et al., "Age-related macular degeneration," N Engl J Med. 2008; 358:2606-17.
Johnson et al., "Drusen-associated degeneration in the retina," Invest Ophthalmol Vis Sci. 2003;44:4481-488.
Brown et al., "Ranibizumab versus verteporfin for neovascular age-related macular degeneration," N Engl J Med. Oct. 5, 2006;355(14):1432-44.
Janoria et al.,"Novel approaches to retinal drug delivery," Expert Opinion on Drug Delivery. Jul. 2007, vol. 4, No. 4, pp. 371-388.
Ghate & Edelhauser, "Ocular drug delivery," Expert Opin Drug Deliv. Mar. 2006;3(2):275-87.
Bourges et al., "Intraocular implants for extended drug delivery: therapeutic applications," Adv Drug Deliv Rev. Nov. 15, 2006;58(11):1182-202. Epub Sep. 22, 2006.
Gomes Dos Santos et al., "Intraocular delivery of oligonucleotides," Curr Pharm Biotechnol. Feb. 2005;6(1):7-15.
Guerin et al., "Recovery of photoreceptor outer segment length and analysis of membrane assembly rates in regenerating primate photoreceptor outer segments," Invest Ophthalmol Vis Sci. 1993;34(1):175-183.
Lewis et al., "Changes in the organization and expression of cytoskeletal proteins during retinal degeneration induced by retinal detachment," Invest Ophthalmol Vis Sci. 1995;36(12):2404-2416.
Heinrich et al., "Principles of interleukin (IL)-6-type cytokine signalling and its regulation," Biochem J. 2003;374(Pt 1):1-20.
Zacks et al., "Activation of signaling pathways and stress-response genes in an experimental model of retinal detachment," Invest Ophthalmol Vis Sci. 2006;47(4):1691-1695.
Hauswirth et al., "Production and purification of recombinant adeno-associated virus," Methods Enzymol 2000;316:743-761.
Zolotukhin et al., "Production and purification of serotype 1, 2, and 5 recombinant adeno-associated viral vectors," Methods 2002;28:158-167.
Leonard et al., "XIAP protection of photoreceptors in animal models of retinitis pigmentosa," PLoS ONE 2007;2: e314.
Lewis GP et al., "The ability of rapid retinal reattachment to stop or reverse the cellular and molecular events initiated by detachment," Invest Ophthalmol Vis Sci 2002;43:2412-2420.
Zou et al., "Lack of Fas antagonism by Met in human fatty liver disease," Nat Med. Sep. 2007;13(9):1078-85.
Al-Ubaidi et al., "Bilateral retinal and brain tumors in transgenic mice expressing simian virus 40 large T antigen under control of the human interphotoreceptor retinoid-binding protein promoter," J Cell Biol, 1992; 119(6):1681-1687.

* cited by examiner mMET = mutant peptide (dissolved in DMSO)
MET = 12-mer that blocks FAS receptor (also dissolved in DMSO)
DMSO = control where the solvent DMSO only is injected

A

METHODS OF INHIBITING PHOTORECEPTOR APOPTOSIS

The present application is a divisional of pending U.S. patent application Ser. No. 12/716,986 filed Mar. 3, 2010, which claims priority to U.S. Provisional Application Ser. No. 61/157,079, filed Mar. 3, 2009, and U.S. Provisional Application Ser. No. 61/254,082, filed Oct. 22, 2009, which are herein incorporated by reference in their entireties.

FIELD OF THE INVENTION

The present invention provides methods to prevent photoreceptor death. In particular, the present invention provides peptides which prevent FAS-mediated photoreceptor apoptosis.

BACKGROUND OF THE INVENTION

Apoptosis (programmed cell death) plays a central role in the development and homeostasis of all multi-cellular organisms. Alterations in apoptotic pathways have been implicated in many types of human pathologies, including developmental disorders, cancer, autoimmune diseases, as well as neurodegenerative disorders, and retinal degradation. It is a tightly regulated pathway governing the death processes of individual cells and can be initiated either extrinsically or intrinsically. The latter is an intracellular mechanism triggered by the mitochondria while the former involves the interaction of a 'death receptor' with its corresponding ligand at the cell membrane.

Thus, the programmed cell death pathways have become attractive targets for development of therapeutic agents. In particular, since it is conceptually easier to kill cells than to sustain cells, attention has been focused on anti-cancer therapies using pro-apoptotic agents such as conventional radiation and chemotherapy. These treatments are generally believed to trigger activation of the mitochondria-mediated apoptotic pathways. However, these therapies lack molecular specificity, and more specific molecular targets are needed.

Retinal detachment (RD), defined as the separation of the neurosensory retina from subjacent retinal pigment epithelium (RPE), results in the apoptotic death of photoreceptor cells (Cook et al. 1995; 36(6):990-996; Hisatomi et al. Curr Eye Res. 2002; 24(3):161-172; Zacks et al. Invest Ophthalmol Vis Sci. 2003; 44(3):1262-1267. Yang et al. Invest Ophthalmol Vis Sci. 2004; 45(2):648-654; herein incorporated by reference in their entireties). Rodent and feline models of RD have demonstrated the activation of pro-apoptotic pathways nearly immediately after the retina becomes separated from the RPE (Cook et al. 1995; 36(6):990-996; Hisatomi et al. Curr Eye Res. 2002; 24(3):161-172; Zacks et al. Invest Ophthalmol Vis Sci. 2003; 44(3):1262-1267. Yang et al. Invest Ophthalmol Vis Sci. 2004; 45(2):648-654; herein incorporated by reference in their entireties). Histological markers of apoptosis such as terminal deoxynucliotidyl transferase nick end label (TUNEL) staining reach a peak at approximately three days after RD, with apoptotic activity and progressive cell death persisting for the duration of the detachment period. Clinical experience in the repair of retinal detachments, however, has demonstrated that there is a window of opportunity for repair with preservation of good visual acuity. Retrospective case series have demonstrated that significant numbers of patients with macula-off RDs repaired within 5-10 days after onset of detachment can retain relatively good visual function, but that the visual acuity drops significantly as the time between detachment and repair extends (Burton. Trans Am Ophthalmol Soc. 1982; 80:475-497; Ross et al. Ophthalmology. 1998; 105(11):2149-2153; Hassan et al. Ophthalmology. 2002; 109(1):146-152; herein incorporated by reference in their entireties). The delayed time between the activation of pro-apoptosis pathways and the clinical onset of visual loss suggests that intrinsic neuroprotective factors may become activated within the neural retina, and may serve to counter-balance the effects of the pro-apoptotic pathways activated by retinal-RPE separation.

SUMMARY

In some embodiments, the present invention provides a method of inhibiting photoreceptor apoptosis comprising administering a photoreceptor protective composition. In some embodiments, the photoreceptor protective composition comprises photoreceptor protective polypeptide or a nucleic acid encoding a photoreceptor protective polypeptide. In some embodiments, the photoreceptor protective polypeptide comprises IL-6 or a fragment thereof. In some embodiments, the photoreceptor protective polypeptide comprises XIAP or a fragment thereof. In some embodiments, the photoreceptor protective polypeptide comprises MET or a fragment thereof. In some embodiments, the fragment of MET comprises MET12. In some embodiments, the fragment of MET comprises at least 70% (e.g., at least 80%, 85%, 90%, 95%) sequence similarity to MET12. In some embodiments, the photoreceptor apoptosis comprises FAS-mediated photoreceptor apoptosis. In some embodiments, the photoreceptor protective composition is administered to a population of cells. In some embodiments, the photoreceptor protective composition is administered in an amount sufficient to attenuate cell death within the population of cells. In some embodiments, the photoreceptor protective polypeptide is administered to a subject. In some embodiments, the subject suffers from retinal detachment. In some embodiments, the subject is at risk of retinal detachment. In some embodiments, the photoreceptor protective composition is administered in an amount sufficient to attenuate cell death within the subject.

In some embodiments, the present invention provides a method of increasing photoreceptor survival comprising administering a photoreceptor protective composition. In some embodiments, increasing photoreceptor survival comprises inhibiting photoreceptor apoptosis. In some embodiments, the photoreceptor protective composition comprises photoreceptor protective polypeptide or a nucleic acid encoding a photoreceptor protective polypeptide. In some embodiments, the photoreceptor protective polypeptide comprises IL-6 or a fragment thereof. In some embodiments, the photoreceptor protective polypeptide comprises XIAP or a fragment thereof. In some embodiments, the photoreceptor protective polypeptide comprises MET or a fragment thereof. In some embodiments, the fragment of MET comprises MET12. In some embodiments, the fragment of MET comprises at least 70% sequence similarity to MET12. In some embodiments, the photoreceptor apoptosis comprises FAS-mediated photoreceptor apoptosis. In some embodiments, the photoreceptor protective composition is administered to a population of cells. In some embodiments, the photoreceptor protective composition is administered in an amount sufficient to attenuate cell death within said population of cells. In some embodiments, the photoreceptor protective composition is administered in an amount sufficient to enhance photoreceptor survival within said population of cells. In some embodiments, the photoreceptor protective composition is administered to a subject. In some embodiments, the subject suffers from an ocular condition, disease, or condition or disease affecting ocular health. In some embodiments, the subject is at risk of an ocular condition, disease, or condition or disease affecting ocular health. In some embodiments, the ocular condition, disease, or condition or disease affecting ocular health comprises retinal detachment, macular degeneration, retinitis pigmentosa, occular inflammation, autoimmune retinopathy, trauma, cancer, tumor, uveitis, hereditary retinal degeneration, diabetic retinopathy, choroidal neovascularization, retinal ischemia, pathologic myopia, angioid streaks, macular edema, or central serous chorioretinopathy. In some embodiments, the ocular condition, disease, or condition or disease affecting ocular health comprises retinal detachment. In some embodiments, the ocular condition, disease, or condition or disease affecting ocular health comprises macular degeneration. In some embodiments, the photoreceptor protective composition is administered in an amount sufficient to attenuate cell death within said subject. In some embodiments, the photoreceptor protective composition is administered in an amount sufficient to enhance photoreceptor survival within said subject.

In some embodiments, the present invention provides a composition comprising a photoreceptor protective composition and a pharmaceutical carrier configured for optical delivery. In some embodiments, the photoreceptor protective composition comprises a photoreceptor protective polypeptide or a nucleic acid encoding a photoreceptor protective polypeptide. In some embodiments, the photoreceptor protective polypeptide comprises IL-6 or a fragment thereof. In some embodiments, the photoreceptor protective polypeptide comprises XIAP or a fragment thereof. In some embodiments, the photoreceptor protective polypeptide comprises MET or a fragment thereof. In some embodiments, the fragment of MET comprises MET12. In some embodiments, the fragment of MET comprises at least 70% (e.g., at least 80%, 85%, 90%, 95%) sequence similarity to MET12. In some embodiments, the photoreceptor apoptosis comprises FAS-mediated photoreceptor apoptosis. In some embodiments, the pharmaceutical carrier is configured for injection into the eye of a subject. In some embodiments, the pharmaceutical carrier is configured for subretinal injection. In some embodiments, the pharmaceutical carrier is configured for topical application onto the eye of a subject.

In some embodiments, the present invention comprises a kit comprising a photoreceptor protective composition and one or more addition compositions. In some embodiments and additional compositions comprises, a photoreceptor protective composition, pharmaceutical carrier, drug, pain reliever, anesthetic, antiapoptotic agent, etc. In some embodiments, a kit comprises one or more photoreceptor protective composition and other agents configured for co-administration to cells or a subject.

BRIEF DESCRIPTION OF THE DRAWINGS

The foregoing summary and detailed description is better understood when read in conjunction with the accompanying drawings which are included by way of example and not by way of limitation.

DEFINITIONS

Figure 1:
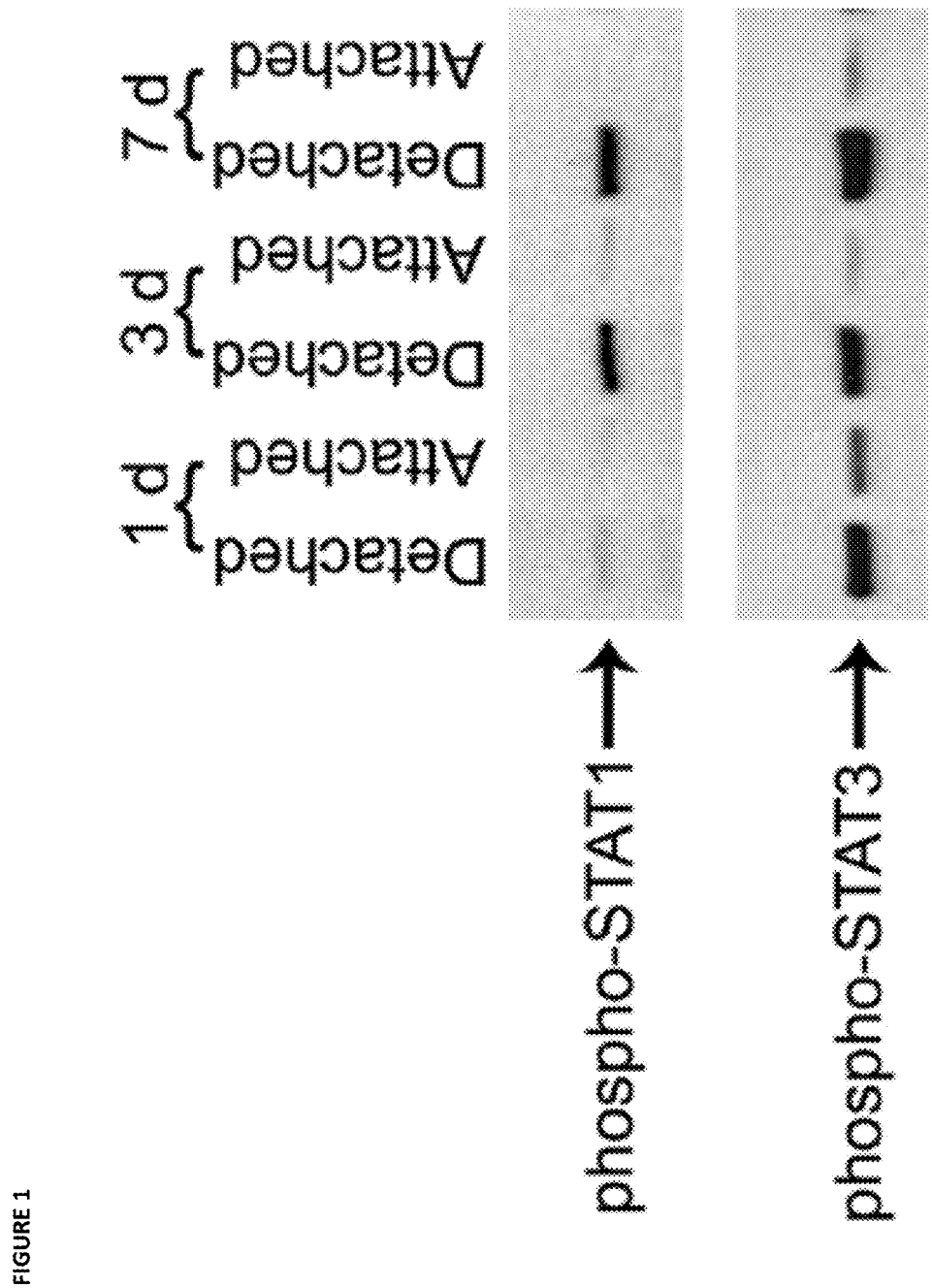
FIG. 1 shows Western blot analysis of levels of activated forms of STAT1 and STAT3 in attached and detached retinas. Leftmost 2 lanes: One day after detachment. Middle 2 lanes: Three days after detachment. Rightmost 2 lanes: Seven days after detachment. Retina-RPE separation was created in the left eye. Attached retina was obtained from the contralateral eye of the same animal. Equal loading was verified across all lanes.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 12 residue oligonucleotide is referred to as a "12-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "effective amount" refers to the amount of a composition (e.g., photoreceptor protective composition) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administer" refer to the administration of at least two agent(s) (e.g., photoreceptor protective peptides, oligonucleotides coding for a photoreceptor protective composition, and one or more other agents) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "pharmaceutical composition" refers to the combination of an active agent (e.g., photoreceptor protective composition) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

DETAILED DESCRIPTION OF EMBODIMENTS

Experiments performed during development of embodiments of the present invention demonstrate that IL-6 is a controller of photoreceptor apoptosis after separation of the neurosensory retina from the underlying RPE. Inhibition of IL-6 with genetic ablation or via administration of an IL-6 neutralizing antibody significantly increased the rate of photoreceptor apoptosis. One month after detachment, both the IL-6−/− mice and the rats receiving subretinal IL-6 NAB had significantly decreased ONL cell counts compared to their respective controls. These data indicate that IL-6 is necessary for the survival of photoreceptors after detachment from the RPE.

Experiments were performed during development of embodiments of the present invention examining the effect of increasing IL-6 levels had mixed effects, depending on the time point examined and the assay measured. When compared to injection of vehicle only, subretinal injection of exogenous IL-6 did not significantly affect the percentage of TUNEL positive cells 3 days after RD, but did significantly increase the number of photoreceptors that survived longer term detachments. Subretinal IL-6 levels in patients with RD are higher than in the vitreous of controls, and the amount of subretinal IL-6 in patients with RD is highest at 5-8 weeks following RD (Bakunowicz-Lazarczyk et al. Ophthalmologica. 1999; 213(1):25-29, herein incorporated by reference in its entirety). IL-6 signals through a combination of its ligand binding subunit (gp80, also known as IL-6R) and a common signal transducing subunit (gp130) (Heinrich et al. Ann NY Acad Sci. 1995; 762:222-236, herein incorporated by reference in its entirety). Administration of exogenous IL-6 alone does not have as much anti-apoptotic activity as administration of IL-6 in conjunction with a soluble form of IL6-R (Inomata et al. Biochem Biophys Res Commun 2003; 302(2):226-232, Curnow et al. J Immunol. 2004; 173(8): 5290-5297, herein incorporated by reference in their entireties).

Despite the activation of endogenous IL-6, there is still a relatively linear rate of cell loss. The rate of this death is significantly decreased by the addition of exogenous IL-6. There was significantly greater preservation of photoreceptors in the group of rats treated with exogenous IL-6 at the time of detachment compared to the control group at the 1 month after RD, the difference was lost 2 months after RD due to accelerated photoreceptor loss in the exogenous IL-6 group in the second month. Reinjection of exogenous IL-6 at the one-month time point suggests that the duration of the effect of IL-6 can be extended, by allowing for a greater therapeutic "window of opportunity" to achieve retinal-RPE re-attachment.

Retinal detachments are often present for an unknown duration of time prior to presenting to the ophthalmologist. Delay of initial subretinal injection of exogenous IL-6 by 2 weeks from the creation of the detachment still allowed significantly greater preservation of photoreceptors 1 month after detachment as compared to controls, indicating that IL-6 may still be useful in preserving photoreceptors despite delayed presentation of patients. The effect of a single injection of IL-6 2 weeks after retinal-RPE separation lasted for 2 weeks.

IL-6 is known to be a strong activator of the Janus kinase (JAK)/signal transducer and activator of transcription (STAT) pathway (Samardzija et al. FASEB J. 2006; 20(13):2411-2413, herein incorporated by reference in its entirety). Retinal-RPE separation potently activates STAT1 and STAT3. STAT1 is associated with tumor suppression and pro-apoptotic activity whereas STAT3 is predominantly associated with cellular proliferation and considered to be anti-apoptotic (Samardzija et al. FASEB J. 2006; 20(13):2411-2413, Aaronson et al. Science. 2002; 296(5573):1653-1655. Stephanou et al. Int J Exp Pathol. 2003; 84(6):239-244, Stephanou et al. Growth Factors. 2005; 23(3):177-182, Battle et al. Curr Mol Med. 2002; 2(4):381-392, herein incorporated by reference in their entireties). The IL-6 effect is mediated predominantly through STAT3 and not STAT1. Modulation of apoptotic pathways by STATs may be though the downstream transcriptional regulation of factors that trigger cell death, such as FAS and caspases, or factors that promote cell survival, such as Bcl-xL and FLICE (FADD (Fas-associated death domain)-like interleukin-1β-converting enzyme) inhibitory protein (FLIP) (Haga et al. J Clin Invest. 2003; 112(7):989-998, Budd et al. Nat Rev Immunol. 2006; 6(3):196-204, herein incorporated by reference in their entireties). FLIP is an enzymatically inactive homologue of caspase-8 that can compete with caspase-8 for recruitment to death-inducing signaling complexes (DISCs), and thus acts as a dominant negative inhibitor of apoptosis. 34 IL-6 may stabilize protein levels of FLIP as FLIP is more rapidly degraded in IL-6−/− mice (Kovalovich et al. J Biol Chem. 2001; 276(28):26605-26613, herein incorporated by reference in its entirety).

Studies have shown that IL-6 may protect against retinal degeneration induced by a range of insults including ischemia-reperfusion injury, NDMA toxicity, pressure induced death, and retinal detachment (Sanchez et al. Invest Ophthalmol Vis Sci. 2003; 44(9):4006-4011, Inomata et al. Biochem Biophys Res Commun 2003; 302(2):226-232, Sappington et al. Invest Ophthalmol Vis Sci. 2006; 47(7):2932-2942, herein incorporated by reference in their entireties). The photoreceptor-protective role of IL-6 in the context of retinal-RPE separation suggests that this is a valuable point of therapeutic intervention for improving visual outcome in patients with this type of retinal injury.

Rapid re-attachment is imperative in order to achieve a good visual outcome following retinal detachment. Animal studies, indicate that caspases—the executors of apoptosis—are activated within 24 hours after a detachment. Patients generally do not recover visual acuity of 20/20 if the duration of retinal detachment lasted 5 days or longer (Burton. Trans Am Ophthalmol Soc 1982; 80:475-497, herein incorporated by reference in its entirety). In many disease processes the reapposition of the retina to the RPE cannot be achieved quickly, resulting in the continuous apoptotic death of photoreceptors. The use of photoreceptor protective agents can potentially limit the extent of photoreceptor death until re-attachment can occur.

Experiments performed during development of embodiments of the present invention demonstrate that X-linked inhibitor of apoptosis (XIAP) can protect photoreceptors for at least 2 months of continual detachment. XIAP-treated retinas maintained larger numbers of nuclear layers in the ONL, and their inner and outer segments were better organized. In addition, they stained robustly with an antibody to rhodopsin, suggesting that they remained viable.

The protective effects of XIAP suggest blocking caspases is effective in blocking the cell death pathway. However, we cannot rule out the possibility that XIAP is having other effects in addition to caspase inhibition, although an understanding of the specific mechanism of action is not necessary to practice the present invention and the present invention is not limited to any particular mechanism of action. XIAP has been shown to suppress cell death via other mechanisms. Through its RING zinc finger domain, XIAP has E3 ubiquitin ligase activity and can promote the degradation of proapoptotic proteins (reviewed in 10). XIAP is also involved in the transcriptional activation of prosurvival pathways through TAK1 (Hofer-Warbinek et al. J Biol Chem 2000; 275:22064-22068, Sanna et al. Mol Cell Biol 2002; 22:1754-1766, herein incorporated by reference in their entireties). TAK1 is a mitogen-activated protein kinase kinase kinase (MAPKKK) involved in the activation of both the NF-kB and JNK1 pro-survival pathways. Thus, the ability of XIAP to protect photoreceptors for up to 2 months may be attributed, in part, to the activation or suppression of multiple pathways. The inhibition of caspase activity and the decreased TUNEL counts in XIAP-transfected eyes, however, does support caspase inhibition as a principal mechanism through which XIAP exerts its photoreceptor protective effects.

Experiments performed during development of embodiments of the present invention demonstrate XIAP efficacy in the treatment of retinal detachment. Rapid delivery of XIAP to the site of retinal detachment has the potential to limit the acute damage suffered by photoreceptors, thus buying the patient critical time until successful re-attachment can be achieved Experiments conducted during development of embodiments of the present invention provided a method of inhibiting Fas signaling and preventing photoreceptor apoptosis after retinal detachment. For example, experimental results demonstrated that a small peptide inhibitor of the Fas death receptor blocks caspase activation and increases photoreceptor survival after retina-RPE separation. For example, in an in vitro model of cone photoreceptors, the small peptide Met12 prevents the Fas-dependent activation of caspase 8. Met12 significantly reduced Fas-signaling and photoreceptor apoptosis in an vivo model of experimental retinal detachment.

Retinal detachment activates the Fas-receptor (Zacks et al. Arch Ophthalmol 2007; 125:1389-1395, Zacks et al. IOVS 2004; 45(12):4563-4569.8, herein incorporated by reference in their entireties), and that this event controls activation of the intrinsic cell death pathway in photoreceptors. Photoreceptor apoptosis can be prevented using large molecules, such as neutralizing antibodies, to inhibit the Fas-receptor, or by preventing the detachment-induced increase in the Fas-receptor transcript with inhibitory RNA. Experiments conducted during development of embodiments of the present invention demonstrated that the same significant level of photoreceptor preservation using a small peptide, Met12.

A rodent model was used to investigate molecular mechanisms regulating photoreceptor death after retinal detachment. Further, Fas-Ab treatment activates caspase 8 in 661W cells in vitro in a dose and time-dependent manner, demonstrating that Fas receptor signaling pathway is intact in these cells. The 661W cell line is a functional in vitro model of photoreceptor apoptosis mediated by Fas signaling.

Methods herein demonstrate significant levels of photoreceptor survival after Met12-mediated Fas inhibition. Thus, Fas inhibition by Met12 resulted in significant preservation of photoreceptor cells in vivo. The dose of Met12 that was injected in the subretinal space at the time of retinal detachment may be optimized for complete protection using methods disclosed herein. In 661W cells, where Met12 reached all cells, Met12 treatment resulted in full inhibition of the caspase 8 activation. Subretinal Met12 may not adequately reach detached photoreceptors that are apoptotic. It is contemplated that improved administration of the peptide yields improved photoreceptor survival. Met12 was injected subretinally only during the creation of retina/RPE separation. The amount of Met12 available in the subretinal space most likely decreases with time, thus increasing the number of Fas receptors available for FasL binding. This is similar to what occurs with another neuroprotectant, IL-6. Exogenous IL-6 increases the survival of detached photoreceptors (Chong et al. Invest Ophthalmol Vis Sci. 2008; 49(7):3193-3200, herein incorporated by reference in its entirety). When IL-6 was injected in the subretinal space at the time of detachment, its protective effect on detached photoreceptors lasted for one month. However, re-injection of exogenous IL-6 at the one-month time point extended duration of photoreceptor survival after retina/RPE separation. It is contemplated that an optimal treatment strategy and increased pro-survival effect of Met12 allows for a greater therapeutic "window of opportunity" to achieve the highest photoreceptor survival rate after retinal-RPE re-attachment.

It is contemplated that a population of photoreceptors executes apoptosis independent of Fas death receptor signaling. The separation-induced activation of the mitochondrial apoptotic pathway is only partially controlled by the activation of Fas (Zacks et al. Arch Ophthalmol 2007; 125:1389-1395, herein incorporated by reference in its entirety). It is contemplated that a second and alternate signaling pathway may play a role in stimulating the intrinsic death pathway in photoreceptors. Intrinsic pathway caspases play a critical role in retinal detachment-induced photoreceptor apoptosis (Zadro-Lamoureux et al. Invest Ophthalmol Vis Sci. 2009; 50(3):1448-1453, herein incorporated by reference in its entirety). Delivery of X-linked inhibitor of apoptosis (XIAP) with a recombinant adenoassociated virus inhibited caspase 3 and caspase 9 activities and protected photoreceptors from detachment-induced apoptosis. In addition to the mitochondrial apoptotic pathway, caspase-independent death pathways may play a role in photoreceptor loss after retinal detachment. Activation of the apoptosis-inducing factor (AIF)-dependent death in an experimental rat model of retina-RPE separation results in apoptosis (Hisatomi et al. Am J Pathol. 2001 April; 158(4):1271-1278, Hisatomi et al. 2008 J Clin Invest 118: 2025-2038, herein incorporated by reference in their entireties). Retinal-detachment induced photoreceptor death was reduced in mice carrying hypomorphic mutation of the gene encoding AIF (Hisatomi et al. 2008 J Clin Invest 118: 2025-2038, herein incorporated by reference in its entirety).

In clinical practice, patients generally present with a detachment having already occurred. The animal models of retina-RPE separation show that Fas-pathway activation takes place early and remains elevated throughout the duration of the detachment (Zacks et al. Arch Ophthalmol 2007; 125:1389-1395, Zacks et al. IOVS 2004; 45(12):4563-4569.8). It is contemplated that one utility of photoreceptor-protective therapy could be to help prevent further photoreceptor loss until the retina could be re-attached (e.g., surgically) and normal retina-RPE homeostasis restored. The separation of retina and RPE is also encountered in a broad spectrum of retinal diseases. It is contemplated that the clinical relevance of anti-Fas therapy in photoreceptor survival is not limited to retinal detachment. For example, Fas-mediated apoptosis may play a role in photoreceptor cell death in age-related macular degeneration (AMD) (Dunaief et al. Arch Ophthalmol. 2002; 120(11):1435-1442, herein incorporated by reference in its entirety). Age-related macular degeneration is characterized by progressive degeneration of the RPE and causes outer retinal degeneration and re-organization similar to that which occurs after retinal detachment (Jager et al. N Engl J Med. 2008; 358:2606-17, Johnson et al. Invest Ophthalmol Vis Sci. 2003; 44:4481-488, herein incorporated by reference in their entireties). In the neovascular form of AMD there is also the exudation of fluid under the retina, creating an actual separation of this tissue from the underlying RPE (Jager et al. N Engl J Med. 2008; 358:2606-17, herein incorporated by reference in its entirety). Neovascular AMD can result in prolonged periods of retina-RPE separation and Fas-pathway activation. The utility of anti-Fas treatment would most likely be as an adjunct aimed at extending the survival of photoreceptors while the underlying disorder is being treated (Brown et al. N Engl J Med. 2006 Oct. 5; 355(14):1432-44, herein incorporated by reference in its entirety). Though additional apoptotic pathways may be activated after retina-RPE separation, experiments performed during development of embodiments of the present invention indicate that a significant number of photoreceptors are preserved by inhibiting the Fas death receptor. It is contemplated that combining Met12 treatment with another anti-apoptotic, e.g. XIAP, or with a pro-survival molecule, e.g. IL-6, increases the efficiency of photoreceptor survival.

In some embodiments, the present invention provides compositions, kits, systems, and/or methods to prevent, inhibit, block, and/or reduce photoreceptor cell death. In some embodiments, the present invention inhibits apoptosis of photoreceptors. In some embodiments, photoreceptor death and/or apoptosis is caused by retinal detachment, age-related macular degeneration, trauma, cancer, tumor, inflammation, uveitis, diabetes, hereditary retinal degeneration, and/or a disease affecting photoreceptor cells. In some embodiments, the present invention enhances photoreceptor viability and/or inhibits photoreceptor death (e.g. during retinal detachment and/or is ocular conditions which do not involve retinal detachment. In some embodiments, the present invention finds utility in enhances photoreceptor viability and/or inhibits photoreceptor death in a variety of conditions and/or diseases including, but not limited to macular degeneration (e.g. dry, wet, non-exudative, or exudative/neovascular), ocular tumors, hereditary retinal degenerations (e.g. retinitis pigmentosa, Stargardt's disease, Usher Syndrome, etc), ocular inflammatory disease (e.g. uveitis), ocular infection (e.g. bacterial, fungal, viral), autoimmune retinitis (e.g. triggered by infection), trauma, diabetic retinopathy, choroidal neovascularization, retinal ischemia, retinal vascular occlusive disease (e.g. branch retinal vein occlusion, central retinal vein occlusion, branch retinal artery occlusion, central retinal artery occlusion, etc.), pathologic myopia, angioid streaks, macular edema (e.g. of any etiology), central serous chorioretinopathy. In some embodiments, the present invention comprises administration of a composition to inhibit photoreceptor death (e.g. apoptosis). In some embodiments, a composition comprises a pharmaceutical, small molecule, peptide, nucleic acid, molecular complex, etc. In some embodiments, the present invention provides administration of a photoreceptor protective polypeptide to inhibit photoreceptor apoptosis. In some embodiments, a polypeptide of the present invention can be prepared by methods known to those of ordinary skill in the art. For example, the claimed polypeptide can be synthesized using solid phase polypeptide synthesis techniques (e.g. Fmoc). Alternatively, the polypeptide can be synthesized using recombinant DNA technology (e.g., using bacterial or eukaryotic expression systems). Accordingly, to facilitate such methods, the present invention provides genetic vectors (e.g., plasmids) comprising a sequence encoding the inventive polypeptide, as well as host cells comprising such vectors. Furthermore, the invention provides the polypeptide produced via recombinant methods.

In some embodiments, the present invention provides administration of photoreceptor protective compositions (e.g. photoreceptor protective peptides, polypeptide, small molecules, nucleic acids, nucleic acids encoding protective peptides, etc.). In some embodiments, the present invention provides administration of polypeptides which inhibit apoptosis of photoreceptor cells (e.g. IL-6, XIAP, MET, fragments thereof, etc.). In some embodiments, the present invention provides administration of nucleic acids which encode polypeptides (e.g. IL-6, XIAP, MET, fragments thereof, etc.) which inhibit apoptosis of photoreceptor cells. In some embodiments, administered compositions inhibit apoptotic pathways. In some embodiments, MET polypeptide is administered (e.g. to a subject, cell or cells) as a inhibitor of apoptosis and/or photoreceptor protective peptide. In some embodiments, MET12 polypeptide is administered. In some embodiments, a polypeptide with at least 50% homology to MET or MET12 is administered (e.g. at least 60% homology, at least 70% homology, at least 80% homology, at least 90% homology, at least 95% homology, at least 99% homology, etc.). In some embodiments, a polypeptide with at least 50% homology to IL-6 is administered (e.g. at least 60% homology, at least 70% homology, at least 80% homology, at least 90% homology, at least 95% homology, at least 99% homology, etc.). In some embodiments, a polypeptide with at least 50% homology to XIAP is administered (e.g. at least 60% homology, at least 70% homology, at least 80% homology, at least 90% homology, at least 95% homology, at least 99% homology, etc.). In some embodiments, administering a peptide, nucleic acid, or a drug-like small molecule to a subject or cell inhibits apoptotic pathways, inhibits apoptosis, and/or protects against photoreceptor death.

In some embodiments, polypeptides of the present invention are isolated and/or purified (or substantially isolated and/or substantially purified). Accordingly, the invention provides polypeptide in substantially isolated form. In some embodiments, polypeptides are isolated from other polypeptides as a result of solid phase protein synthesis, for example. Alternatively, polypeptides can be substantially isolated from other proteins after cell lysis from recombinant production. Standard methods of protein purification (e.g., HPLC) can be employed to substantially purify polypeptides.

In some embodiments, the present invention provides a preparation of polypeptides in a number of formulations, depending on the desired use. For example, where the polypeptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc., and the inventive polypeptide can, in some embodiments, be prepared in lyophilized form. Moreover, such preparations can include other desired agents, such as small molecules or even other polypeptides and proteins, if desired. Indeed, the invention provides such a preparation comprising a mixture of different embodiments of the inventive polypeptide (e.g., a plurality of polypeptide species as described herein).

In some embodiments, the present invention also provides a pharmaceutical composition comprising of one or more polypeptides (including mixtures thereof) and a pharmaceutically acceptable carrier. Any carrier which can supply a polypeptide without destroying the vector within the carrier is a suitable carrier, and such carriers are well known in the art. The composition can be formulated for parenteral, oral, or topical administration. For example, a parenteral formulation could consist of a prompt or sustained release liquid preparation, dry powder, emulsion, suspension, or any other standard formulation. An oral formulation of the pharmaceutical composition could be, for example, a liquid solution, such as an effective amount of the composition dissolved in diluents (e.g., water, saline, juice, etc.), suspensions in an appropriate liquid, or suitable emulsions. An oral formulation could also be delivered in tablet form, and could include excipients, colorants, diluents, buffering agents, moistening agents, preservatives, flavoring agents, and pharmacologically compatible excipients. A topical formulation could include compounds to enhance absorption or penetration of the active ingredient through the skin or other affected areas, such as dimethylsulfoxide and related analogs. The pharmaceutical composition could also be delivered topically using a transdermal device, such as a patch, which could include the composition in a suitable solvent system with an adhesive system, such as an acrylic emulsion, and a polyester patch. Compositions could be delivered via eye drops or other topical eye delivery method. Compisitions may be delivered intraocularly, anywhere in the eye including, for example, the vitreous cavity, the anterior chamber, etc. Compisitions may be delivered intravitrealy as is commonly done with intravitreal injections of Lucentis (ranabizumab), Avastin (bevazizumab), triamcinolone acetonide, antibiotics, etc. Compisitions may be delivered periocularly (e.g. to the tissue around the eyeball (globe) but within the bony orbit). Compositions may be delivered via intraocular implant (e.g. gancyclovir implant, fluocinolone implant, etc.). In intraocular implant delivery, devices containing compositions of the present invention are surgically implanted (e.g. within the vitreous cavity), and the drug is released into the eye (e.g. at a predetermined rate). Compositions may be administered using encapsulated cell technology (e.g. by Neurotech) in which genetically modified cells are engineered to produce and secrete compositions of the present invention (e.g. Met 12). Compositions may be delivered via transcleral drug delivery using a device sutured or placed next to the globe that would slowly elute the drug, which would then diffuse into the eye.

In some embodiments, the invention provides a method of employing polypeptides to attenuate the activation of one or more members of the TNFR superfamily, desirably Fas and/or TNFR in photoreceptors and/or retinas. In some embodiments, such method is employed, for example, to inhibit cell death (e.g., apoptosis) in cells and tissues, and it can be employed in vivo, ex vivo or in vitro. Thus, the invention provides for the use of the inventive polypeptide for attenuating cell death (e.g. retinal cell death) in accordance with such methods. For in vitro application, the inventive polypeptide is provided to cells, typically a population of cells (e.g., within a suitable preparation, such as a buffered solution) in an amount and over a time course sufficient to inhibit apoptosis within the cells or to inhibit inflammation. If desired, a controlled population untreated with the inventive polypeptide can be observed to confirm the effect of the inventive polypeptide in reducing the inhibition of cell death or inflammation within a like population of cells.

In some embodiments, the methods of the present invention are employed in vivo. In some embodiments, polypeptides are delivered to a human or animal subject in an amount and at a location sufficient to inhibit or attenuate apoptosis or inflammation within the patient (e.g., within desired tissue). Polypeptide can be formulated into a suitable pharmaceutical composition (e.g., as described above or as otherwise known to those of ordinary skill in the art) for delivery into the subject. The delivery can be local (e.g., by injection or implantation within the desired tissue to be treated) or systemic (e.g., by intravenous or parenteral injection).

In some embodiments, the present invention provides a method for treating patients suffering from such retinal detachment and or retinal disorders and in need of treatment. In some embodiments, a pharmaceutical composition comprising at least one polypeptide of the present invention is delivered to such a patient in an amount and at a location sufficient to treat the disorder or disease. In some embodiments, polypeptides of the present invention (or pharmaceutical composition comprising such) can be delivered to the patient systemically or locally, and it will be within the ordinary skill of the medical professional treating such patient to ascertain the most appropriate delivery route, time course, and dosage for treatment. It will be appreciated that application of the inventive method of treating a patient most preferably substantially alleviates or even eliminates such symptoms; however, as with many medical treatments, application of the inventive method is deemed successful if, during, following, or otherwise as a result of the inventive method, the symptoms of the disease or disorder in the patient subside to a degree ascertainable.

In some embodiments, the present invention provides methods for increasing photoreceptor survival comprising administering a photoreceptor protective pharmaceutical composition. The pharmaceutical compound may be administered in the form of a composition which is formulated with a pharmaceutically acceptable carrier and optional excipients, adjuvants, etc. in accordance with good pharmaceutical practice. The photoreceptor protective pharmaceutical composition may be in the form of a solid, semi-solid or liquid dosage form: such as powder, solution, elixir, syrup, suspension, cream, drops, paste and spray. As those skilled in the art would recognize, depending on the chosen route of administration (e.g. eye drops, injection, etc.), the composition form is determined. In general, it is preferred to use a unit dosage form of the inventive inhibitor in order to achieve an easy and accurate administration of the active pharmaceutical compound. In general, the therapeutically effective pharmaceutical compound is present in such a dosage form at a concentration level ranging from about 0.5% to about 99% by weight of the total composition: i.e., in an amount sufficient to provide the desired unit dose. In some embodiments, the pharmaceutical composition may be administered in single or multiple doses. The particular route of administration and the dosage regimen will be determined by one of skill in keeping with the condition of the individual to be treated and said individual's response to the treatment. In some embodiments, a photoreceptor protective pharmaceutical composition in a unit dosage form for administration to a subject, comprising a pharmaceutical compound and one or more nontoxic pharmaceutically acceptable carriers, adjuvants or vehicles. The amount of the active ingredient that may be combined with such materials to produce a single dosage form will vary depending upon various factors, as indicated above. A variety of materials can be used as carriers, adjuvants and vehicles in the composition of the invention, as available in the pharmaceutical art. Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions.

In some embodiments, photoreceptor protective compositions of the present invention are administered optically, for example, using the techniques described herein, and/or other techniques (e.g. injection, topical administration, etc.) known to those in the art (See, e.g., Janoria et al. Expert Opinion on Drug Delivery. July 2007, Vol. 4, No. 4, Pages 371-388; Ghate & Edelhauser. Expert Opin Drug Deliv. 2006 March; 3(2): 275-87; Bourges et al. Adv Drug Deliv Rev. 2006 Nov. 15; 58(11):1182-202. Epub 2006 Sep. 22; Gomes Dos Santos et al. Curr Pharm Biotechnol. 2005 February; 6(1):7-15; herein incorporated by reference in their entireties.

In some embodiments, photoreceptor protective compositions of the present invention are provided as part of a kit. In some embodiments, a kit of the present invention comprises one or more photoreceptor protective compositions and/or photoreceptor protective pharmaceutical compositions. In some embodiments, a kit comprises a photoreceptor protective composition is configured for co-administration with one or more additional compositions (e.g. pharmaceutical compositions). In some embodiments, one or more photoreceptor protective compositions are co-administered with one or more other agents for effective protection of photoreceptors and/or inhibition of apoptosis.

EXPERIMENTAL

Example 1

Compositions and Methods

Experimental Model of Retinal Detachment

All experiments performed during the development of embodiments of the present invention were performed in accordance with the ARVO Statement for the Use of Animals in Ophthalmic and Vision Research and the guidelines established by the University Committee on Use and Care of Animals of the University of Michigan. Detachments were created in adult male Brown-Norway rats (300-400 g) (Charles River Laboratories, Wilmington, Mass.), wildtype C57BL mice (age 3-6 weeks) (Jackson Laboratory, Bar Harbor, Me.), and IL-6-/- mice on a C57BL background (age 3-6 weeks) (Jackson Laboratory, Bar Harbor, Me.)(Zacks et al. Arch Ophthalmol. 2007; 125(10):1389-1395; herein incorporated by reference in its entirety). Rodents were anesthetized with a 50:50 mix of ketamine (100 mg/mL) and xylazine (20 mg/mL), and pupils were dilated with topical phenylephrine (2.5%) and tropicamide (1%). A 20-gauge microvitreoretinal blade (Walcott Scientific, Marmora, N.J.) was used to create a sclerotomy 2 mm posterior to the limbus, carefully avoiding lens damage. A Glaser subretinal injector (32-gauge tip; BD Ophthalmic Systems, Sarasota, Fla.) was introduced through the sclerotomy into the vitreous cavity and then through a peripheral retinotomy into the subretinal space. Sodium hyaluronate (10 mg/mL) (Pharmacia and Upjohn Co., Kalamazoo, Mich.) was slowly injected to detach the neurosensory retina from the underlying retinal pigment epithelium. Approximately one-third to one-half of the neurosensory retina was detached. Detachments were created in the left eye, leaving the right eye as the control. In some eyes, either 0.15 µg anti-human IL-6 neutralizing antibody (NAB) (R&D Systems, Minneapolis, Minn.) or 15 ng exogenous human IL-6 (R&D Systems, Minneapolis, Minn.) was injected into the subretinal space of the detachment in a 10 µl volume at the time of creation of the detachment or at a subsequent time point. Doses were based on manufacturers' recommendations based on in vitro activity assays.

Western Blot Analysis

Retinas from experimental eyes with detachments and control eyes without detachments were dissected from the RPE-choroid at 3 days after retinal detachment, homogenized, and lysed in buffer containing 10 mM HEPES (pH 7.6), 0.5% IgEPal, 42 mM KCl, 1 mM phenylmethylsulfonyl fluoride (PMSF), 1 mM EDTA, 1 mM EGTA, 1 mM dithiothreitol (DTT), and 5 mM $MgCl_2$ and 1 tablet of protease inhibitors per 10 mL buffer (Complete Mini; Roche Diagnostics GmbH, Mannheim, Germany). The homogenates were incubated on ice and centrifuged at 22,000 g at 4° C. for 60 minutes. The protein concentration of the supernatant was then determined (DC Protein Assay kit; Bio-Rad Laboratories, Hercules Calif.). The protein samples were loaded and run on SDSPage polyacrylamide gels (Tris-HCl Ready Gels; Bio-Rad Laboratories). After electrophoretic separation, the proteins were transferred onto polyvinylidene fluoride (PVDF) membranes (Immobilon-P; Amersham Pharmacia Biotech, Piscataway, N.J.). Protein bands were visualized with Ponceau S staining, and the lanes assessed for equal loading by densitometry of a nonspecific band present across all lanes. Membranes were then immunoblotted for phospho-STAT1 (Tyr701) or phospho-STAT3 (Tyr705) using an immunoblotting kit (PhosphoPlus® Stat1 (Tyr701) Antibody Kit #9170 or PhosphoPlus® Stat3 (Tyr705) Antibody Kit #9130, respectively, Cell Signaling Technology, Danvers, Mass.) according to the manufacturer's instructions using a 1:1000 dilution of the primary antibody.

TUNEL Staining and Histology

At varying intervals after creation of the detachment, the animals were euthanized, and the eyes were enucleated. For TUNEL staining, whole eyes were fixed overnight at 4° C. in phosphate-buffered saline with 4% paraformaldehyde (pH 7.4). The specimens were embedded in paraffin and sectioned at a thickness of 5-6 μm. TUNEL staining was performed on the sections with the ApopTag Fluorescein In Situ Apoptosis Detection Kit according to the manufacturer's instructions (Millipore, Billerica, Mass.). For light microscopic analysis, paraffin sections were stained with 0.5% toluidine blue in 0.1% borate buffer.

Data Analysis

Photoreceptor cell apoptosis was quantified as the percentage of total cells in the outer nuclear layer (ONL) that was TUNEL positive. Three non-overlapping high power fields (40×) at the maximal height of the RD were selected per section and were averaged unless there were less than three non-overlapping high power fields in which case fewer fields were used. One representative section was used per eye. The total number of cells in the ONL was measured in a similar fashion. The total thickness of the retina (measured from the outer edge of the ONL to the inner limiting membrane) was measured in three places in each of three non-overlapping high power fields (40×) at the maximal height of the RD per section and averaged for each eye. Photoreceptor inner and outer segments were not included in the total retinal thickness measurement given variable retraction of these elements after detachment of the neurosensory retina which does not necessarily correlate with post-reattachment viability of the photoreceptors (Guerin et al. Invest Ophthalmol Vis Sci. 1993; 34(1):175-183; Lewis et al. Invest Ophthalmol Vis Sci. 1995; 36(12):2404-2416; herein incorporated by reference in their entireties). For toluidine blue stained specimens, normalization of ONL cell count to the total retinal thickness of each section (i.e., ONL cell count divided by total retinal thickness) was performed to account for possible differences in angles of sectioning and allow for inter-sample comparison. ONL cell counts and total retinal thicknesses in each group of the rat experiments were also normalized to corresponding values of attached retinas in that group to allow inter-sample comparison. For each experimental group, measurements were done on 3 sections from 4-11 eyes, each eye from a separate animal.

Statistical analysis comparing percentage of TUNEL positive cells in the ONL between groups and comparing the ONL cell count/total retinal thickness ratio between groups was performed using 2-tailed Student's t tests without assuming equal variance.

Example 2

Interleukin-6 as a Photoreceptor Neuroprotectant in an Experimental Model of Retinal Detachment The immediately downstream transducers of IL-6 receptor signaling are Signal Transducers and Activators of Transcription (STATs) (Heinrich et al. Biochem J. 2003; 374(Pt 1):1-20, Samardzija et al. FASEB J. 2006; 20(13):2411-2413; herein incorporated by reference in their entireties). In the context of retinal-RPE separation, STAT1 and STAT3 transcript and protein levels are increased (Zacks et al. Invest Ophthalmol Vis Sci. 2006; 47(4):1691-1695, herein incorporated by reference in its entirety). Increased phosphorylation (i.e., activation) of STAT1 and STAT3 in detached retinas compared to attached retinas. Injection of the IL-6 neutralizing antibody into the subretinal space at the time of detachment resulted in approximately a 50% reduction in the level of phosphorylated STAT3. There was not any reduction in the level of phosphorylated STAT1. These data suggest that after retinal-RPE separation, IL-6 effect is mediated predominantly through STAT3 but not STAT1.

Figure 2:
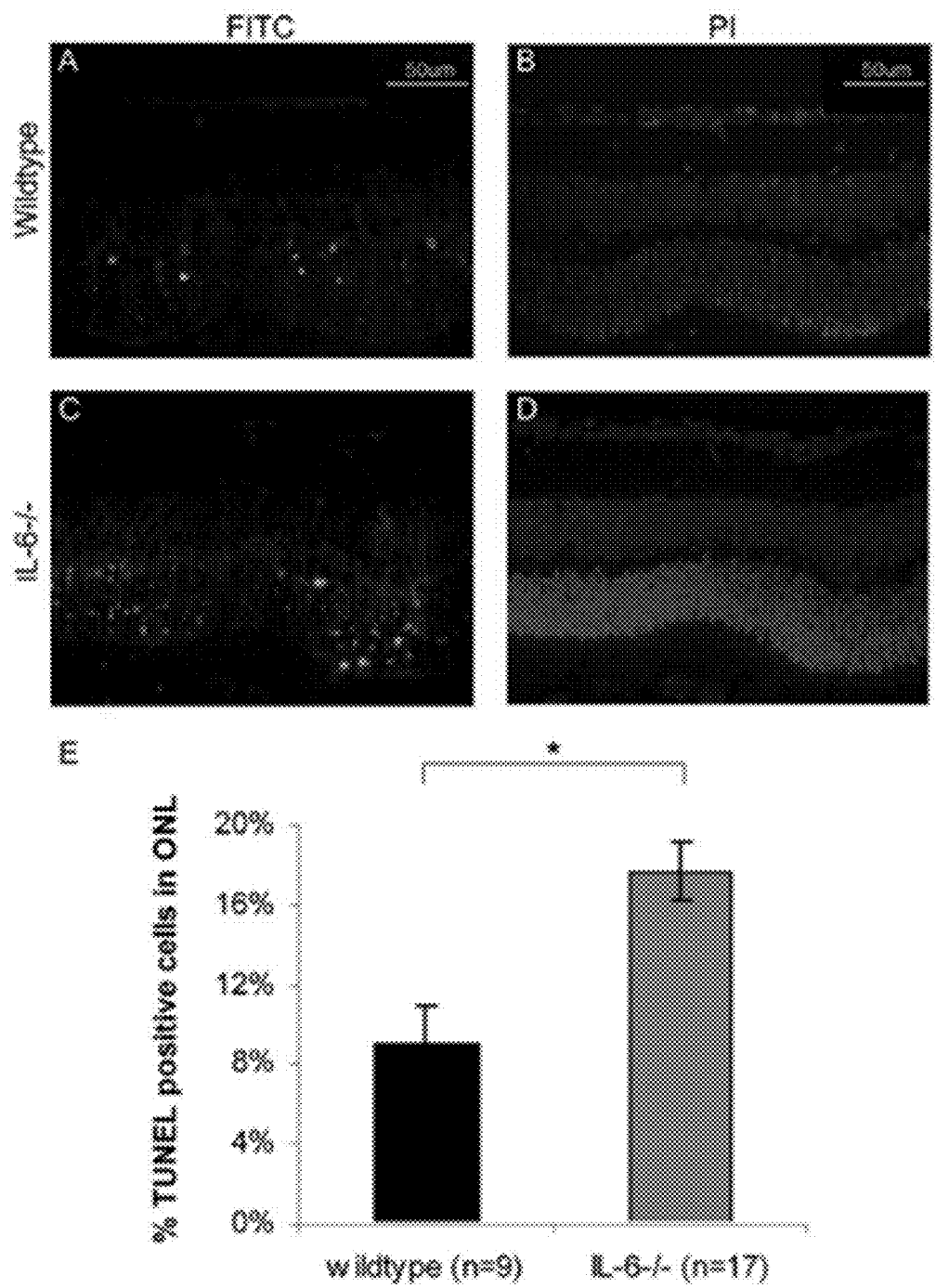
FIG. 2 shows TUNEL staining in wildtype vs. IL6−/− mouse retinas harvested 3 days after detachment. A, B: Wildtype mice. C, D: IL-6−/− mice. A, C: Fluorescein isothiocyanate (FITC) fluorescence of TUNEL positive cells. B, D: Propidium iodide (PI) fluorescence of all nuclei. E: Graph summarizing TUNEL staining of wildtype and IL-6−/− mouse retinas 3 days after detachment. Results are means±standard error of the mean.
Figure 3:
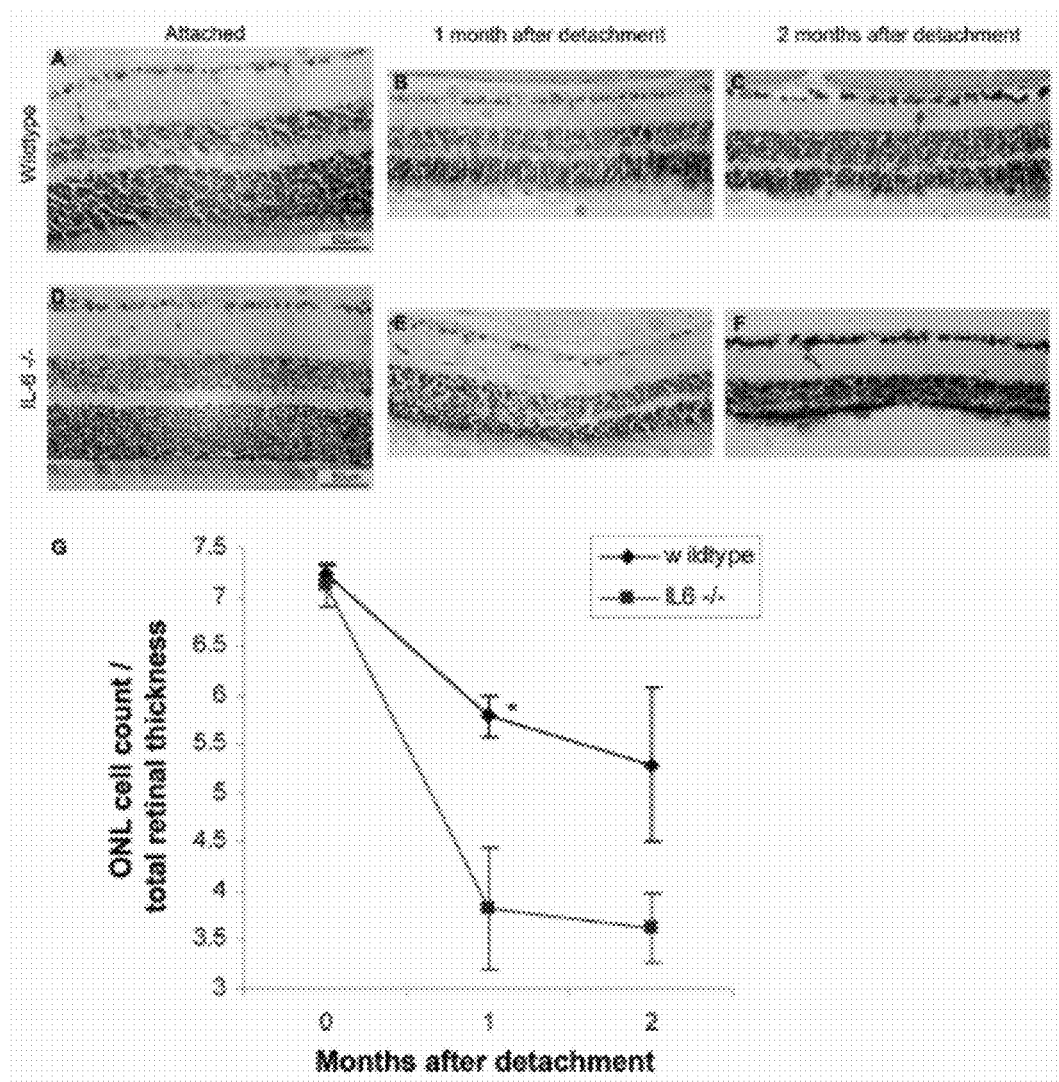
FIG. 3 shows outer nuclear layer cell counts in wildtype vs. IL6−/− mice after retinal detachment. A-C: Wildtype mice. D-F: IL-6−/− mice. A, D: Attached retinas. B, E: Retinas harvested 1 month after creation of the detachment. C, F: Retinas harvested 2 months after creation of the detachment. G: Graph summarizing ONL cell counts/total retinal thickness in wildtype and IL-6−/− mice 1 and 2 months after retinal detachment. Results are means±standard error of the mean.
Figure 4:
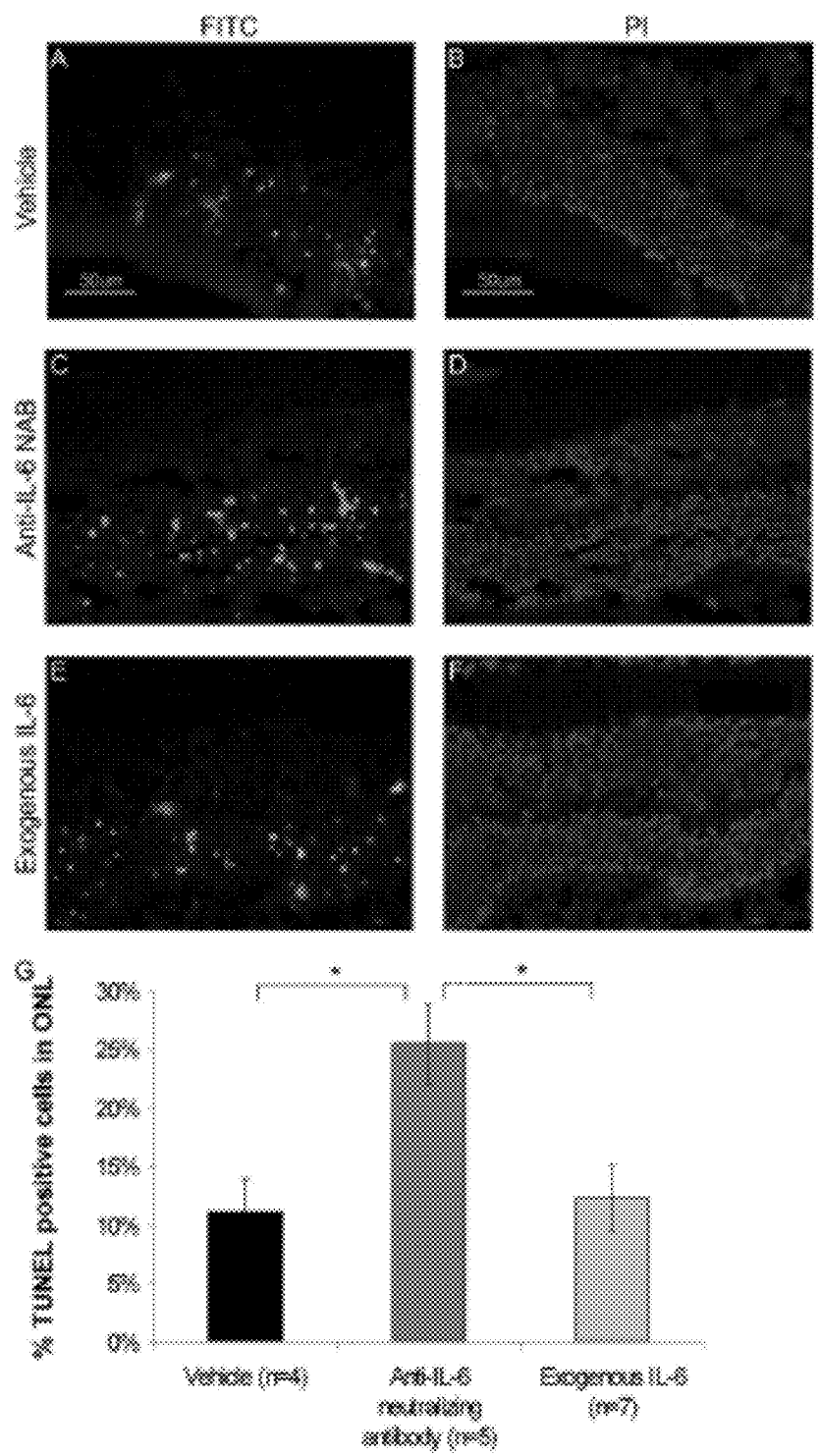
FIG. 4 shows TUNEL staining of detached rat retinas treated with IL-6 neutralizing antibody or exogenous IL-6. A, B: Subretinal injection of vehicle only at the time of creation of the detachment. C, D: Subretinal injection of 0.15 mg anti-IL-6 NAB at the time of creation of the detachment. E, F: Subretinal injection of 15 ng exogenous IL-6 at the time of creation of the detachment. A, C, E: FITC fluorescence of TUNEL positive nuclei. B, D, F: PI fluorescence of all nuclei. G: Graph summarizing effects of subretinal anti-IL-6 NAB and exogenous IL-6 on TUNEL staining of rat retinas 3 days after detachment. Results are means±standard error of the mean.

Experiments were performed during development of embodiments of the present invention in which retinal-RPE separation was created in wildtype C57BL and IL-6-/- mice. Three days after detachment, the eyes were harvested, and apoptosis within the retina was evaluated with TUNEL staining TUNEL positive cells were confined to the ONL of photoreceptors, consistent with prior studies of experimental RD.3 The percentage of TUNEL positive cells in the ONL of detached retinas was significantly greater in the IL-6-/- mice compared to the wildtype mice (SEE FIG. 2). Detachments in wildtype and IL-6-/- mice were created and maintained for 1 and 2 months. Eyes were then harvested for toluidine blue staining. The ONL cell count/total retinal thickness ratio was very similar between attached retinas of wildtype mice and attached retinas of IL-6-/- mice (SEE FIG. 3). There was a decline in the normalized ONL cell count at the 1 month time point for both wildtype and IL-6-/- mice as compared to attached retinas at time zero, but the rate of photoreceptor cell death was significantly higher in the IL-6-/- mice (SEE FIG. 3). Two months after detachment, there was further decline in the ONL cell count/total retinal thickness ratio. The IL-6-/- group had lower final ONL cell counts that wild-type animals (SEE FIG. 3). Retinal-RPE separation was created in Brown Norway rats and either vehicle only or vehicle plus 0.15 μg anti-human IL-6 NAB was injected subretinally at the time of detachment. TUNEL staining of rat eyes 3 days after detachment revealed significantly higher percentages of TUNEL positive cells in the ONL of retinas treated with anti-IL-6 NAB compared to those treated with vehicle only (SEE FIG. 4 A-D, G). 15 ng of recombinant IL-6 was injected subretinally at the time of creation of the detachment. The percentage of TUNEL positive cells in the group of rats treated with subretinal exogenous IL-6 was no different than that of rats treated with vehicle alone, but still significantly less than that of rats treated with subretinal anti-IL-6 NAB (SEE FIG. 4).

Figure 5:
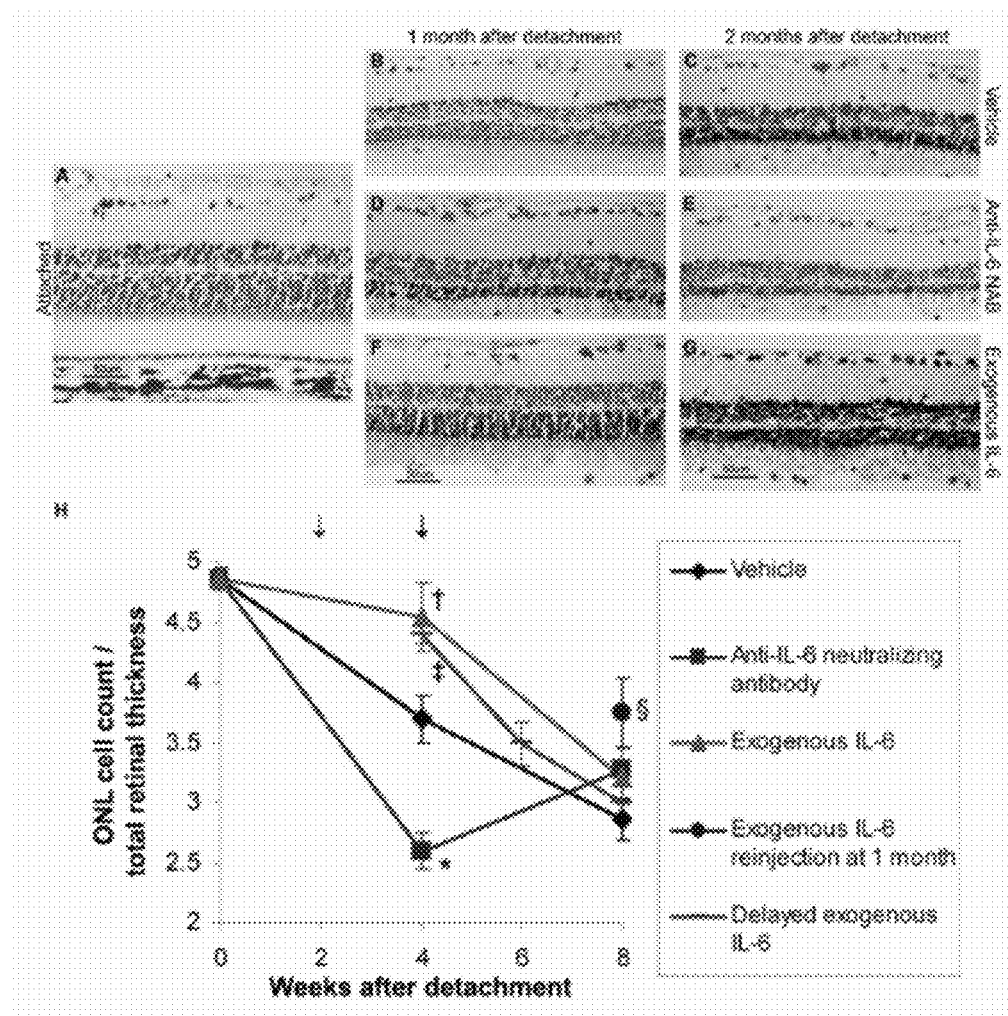
FIG. 5 shows Effects of IL-6 neutralizing antibody vs. exogenous IL-6 on rat retina outer nuclear layer cell counts. A: Attached retina. B, C: Retina harvested 1 and 2 months after subretinal injection of vehicle only at the time of creation of the detachment, respectively. D, E: Retina harvested 1 and 2 months after subretinal injection of 0.15 μg anti-IL-6 NAB at the time of creation of the detachment, respectively. F, G: Retina harvested 1 and 2 months after subretinal injection of 15 ng exogenous IL-6 at the time of creation of the detachment, respectively. H: Graph summarizing effects of subretinal anti-IL-6 NAB and exogenous IL-6 on outer nuclear layer cell count of rat retinas 1 and 2 months after retinal detachment. Results are means±standard error of the mean.

When the period of retinal-RPE separation was extended to 4 and 8 weeks, subretinal injection of anti-IL-6 NAB at the time of detachment resulted in significantly lower normalized ONL cell counts 4 weeks after detachment compared to subretinal injection of vehicle only (SEE FIG. 5B, D, H). In contrast, subretinal administration of exogenous IL-6 at the time of detachment resulted in significantly higher ONL cell count/total retinal thickness ratios 4 weeks after detachment compared to controls injected with vehicle only (SEE FIG. 5B, F, H). Subretinal administration of exogenous IL-6 appeared to slow the rate of photoreceptor cell loss during the first month after detachment, but the rate accelerated during the second month after detachment such that the protective benefit of exogenous IL-6 was lost, and the ONL cell count/total retinal thickness ratios were similar between groups treated with vehicle only, anti-IL-6 NAB, and exogenous IL-6 8 weeks after detachment (SEE FIG. 5C, E, G, H).

Rats were injected with exogenous IL-6 at the time of creation of the detachment followed by a second injection of the same dose of exogenous IL-6 at 4 weeks after detachment. At eight weeks after creating the RD, the ONL cell count/total retinal thickness was still significantly higher in animals with repeat IL-6 injection at 4 weeks than in control animals (SEE FIG. 5H).

Retinal-RPE separation was created as per the above protocol, followed by injection of exogenous IL-6 two weeks after creation of the RD. Eyes were harvested 4, 6, and 8 weeks following detachment (i.e., 2, 4, and 6 weeks following subretinal IL-6 injection, respectively) and stained with toluidine blue. The ONL cell count/total retinal thickness was minimally lower in the group in which IL-6 injection was delayed 2 weeks as compared to the group in which IL-6 injection was administered at the time of creation of the detachment, and was significantly higher than control animals (SEE FIG. 5H). As with the animals treated with IL-6 at the time of retinal-RPE separation, the effect of delayed IL-6 injection seemed to diminish after the 4 week post-detachment time point, with the number of ONL cells reaching the control values by 8 weeks after detachment.

Example 3

Compositions and Methods Relating to X-Link Inhibitor of Apoptosis

Animals

Adult male, Brown Norway rats, at least 6 weeks of age, were purchased from Harlan (Indianapolis, Ind.) and Charles River Laboratories (Wilmington, Mass.). Animals were maintained under standard laboratory conditions and all procedures conformed to both the ARVO Statement for the Use of Animals in Ophthalmic and Vision Research and the guidelines of the University of Ottawa Animal Care and Veterinary Service. Rats were divided into two groups, with one group receiving XIAP gene therapy and the other receiving the green fluorescent protein (GFP) control.

Construction of the Recombinant Adeno-Associated Virus (rAAV) Vectors

A cDNA construct encoding the full-length, open-reading frame of human XIAP with an Nterminal hemagglutinin (HA) tag was inserted into a pTR vector under the control of the chicken β-actin promoter. A GFP construct was similarly generated for use as a surgical and viral control. X-linking inhibitor of apoptosis (XIAP) viral transgene expression was enhanced by inserting a woodchuck hepatitis virus post-transcriptional regulatory element (WPRE) in the 3' untranslated region of the construct. Serotype 5 rAAV was generated (Hauswirth et al. Methods Enzymol 2000; 316:743-761, Zolotukhin et al. Methods 2002; 28:158-167, herein incorporated by reference in their entireties) and purified (Leonard et al. PLoS ONE 2007; 2:e314, herein incorporated by reference in its entirety). Viral titers were $2.33 \times 10^{12}$ physical particles/ml for rAAV-GFP and $1.87 \times 10^{13}$ physical particles/ml for rAAVXIAP. Ratios of physical to infectious particles were less than 100.

Subretinal Injections

An injection of rAAV carrying either XIAP or GFP was delivered to the subretinal space of the left eye of each rat. The right eye served as an untreated control. Animals were anesthetized by 2% isofluorane gas inhalation. Eyes were dilated using 1% tropicamide (Mydriacyl; Alcon Canada, Mississauga, ON, Canada) and 2.5% phenylephrine hydrochloride (Mydfrin; Alcon). Proparacaine hydrochloride drops (0.5%, Alcaine, Alcon) were administered as a local anesthetic. Pain management was achieved by buprenorphine injection (0.04 mg/kg). To maintain lubrication throughout the procedure, 0.3% hypromellose (Genteal gel; Novartis Pharmaceuticals Inc., Mississauga, ON, Canada) was applied to the eye. Subretinal injections were performed by creating a sclerotomy approximately 2 mm posterior to the limbus with a 20-gauge V-lance knife (Alcon). Care was taken to avoid lens contact as this could induce cataract development. A cover slip coated with Genteal was placed on top of the eye to provide magnification and visualization of the back of the eye. A 33-gauge blunt needle attached to a 10 ml syringe (Hamilton Company, Reno, Nev.) was inserted through the scleral puncture, guided lateral to the lens, and inserted through the retina. A 2 µL volume of rAAV-XIAP or rAAV-GFP combined with fluorescein tracer (50:1 v/v) was delivered to the sub retinal space of the eye. The fluorescein allowed for immediate visualization and evaluation of the injection location, allowing ascertainment of a successful subretinal delivery. Injections were delivered in a consistent manner between the 12:00 and 2:00 position. Post-surgical care consisted of administration of the antibiotic 0.3% ciprofloxacin hydrochloride (Ciloxan; Alcon), and a non-steroidal anti-inflammatory drug 0.03% flurbiprofen sodium (Ocufen; Allergan, Irvine, Calif.) for five days postinjection.

Retinal Detachment

Approximately two weeks following viral injections, a retinal detachment was performed in the left eye of each rat. The detachments were created by injecting 10 mg/mL sodium hyaluronate (Healon; AMO, Santa Ana, Calif.) into the subretinal space near the site of the viral injection. Approximately one-third to one-half of the retina was detached, leaving the remaining attached portion to serve as an internal control. Animals were sampled at 24 hours, 3 days, and 2 months after detachment.

Caspase Assays—24 Hours after Detachment

Twenty-four hours after the creation of the detachment, the intact right retinas (internal control) and the detached portion of the left retinas were harvested from XIAP (N=15) and GFP (N=15) animals, and protein was extracted (Zacks et al. Invest Ophthalmol Vis Sci 2004; 45:4563-4569, herein incorporated by reference in its entirety). Caspase 9 activity was measured using a Caspase 9 Colorimetric Assay Kit (BioVision Research Products, Mountain View, Calif.), as per the manufacturer's instructions. This assay is based on the detection of the chromophore p-nitroanilide (pNA) following cleavage from the labeled substrate LEHD-pNA. Caspase 3 activity was measured using a Caspase 3 Colorimetric Assay kit (Chemicon International, Billerica, Mass.), as per manufacturer's instructions. This assay is based on cleavage of the pNADEVD substrate by activated caspase 3.

Tissue Fixation and Processing

Rats were administered a lethal injection of Euthansol and were subsequently perfused with 4% paraformaldehyde (PFA) in order to preserve tissue structure. Left eyes were scored with a white hot needle to enable orientation during nucleation and embedment. Eyes were punctured with a needle to allow penetration of the fixative and were placed in 4% PFA overnight. The samples were then taken through a series of dehydration steps ending with embedment in paraffin. Eyes were sectioned at 10 mm for histological analysis.

Histological Analysis

Hematoxylin and eosin (H&E) staining was performed on 10 mm sections to locate retinal detachments. Once a detachment was identified, subsequent slides were subjected to immunohistochemical analysis in order to confirm the presence of XIAP or GFP. XIAP was detected using an anti-HA mouse IgG primary antibody (Roche Applied Science, Laval, QC), followed by a goat anti-mouse IgG secondary antibody (Jackson ImmunoResearch Laboratories, Inc., West Grove, Pa.). GFP was detected using an anti-GFP rabbit IgG (Invitrogen, Eugene, Oreg.) followed by a goat anti-rabbit IgG (Invitrogen, Eugene, Oreg.). Rhodopsin was detected with the B630 monoclonal antibody. 27 Slides were counterstained with the nuclear stain 4',6'-diamindino-2-phenylindole dihydrochloride (DAPI). Images were obtained using a Zeiss Axioskop light microscope with a Zeiss AxioCam HRc camera. Terminal uridine deoxynucleotidyl transferase dUTP nick end labeling (TUNEL)

Staining

TUNEL was used to compare levels of apoptosis in detached regions of XIAP-treated versus GFP-treated samples 3 days after detachment. TUNEL-positive cells were detected using the Apoptag Peroxidase in situ Apoptosis Detection Kit (Chemicon, Temecula, Calif.). In order to eliminate observer bias, TUNEL-positive cells were detected using a program developed with the mathematical software MATLAB (version R2007a, The Mathworks Inc.). The program analyzed Photoshop images (Adobe Systems Inc.) of the outer nuclear layer (ONL) of detached retinas. A TUNEL-positive nucleus was identified, and its RGB values were recorded. The software scanned the image on a pixel-by-pixel basis to determine the number of pixels that fell within two standard deviations of the RGB value s of the positive nucleus. The number of "TUNEL-positive" pixels was then divided by the total tissue pixels to yield a ratio of "TUNEL-positive" pixels for that section.

Retinal Thickness Comparison

Eyes that were sampled at 2 months after the detachment were processed for histological analysis. Images were taken of 10 μm sections stained with H&E. Thickness of the ONL was measured as a ratio of the number of nuclear layers across the ONL of the detached retina divided by the number of nuclear layers across the ONL of the attached portion of the same retina. Retinal thickness varies with distance from the optic nerve, the thickness of the inner nuclear layer (INL) was used as a control to ensure that ONL measurements were taken at the same distance from the optic nerve head. For both attached and detached regions, at least four counts were taken from each animal and averaged.

Example 4

X-Link Inhibitor of Apoptosis

Figure 6:
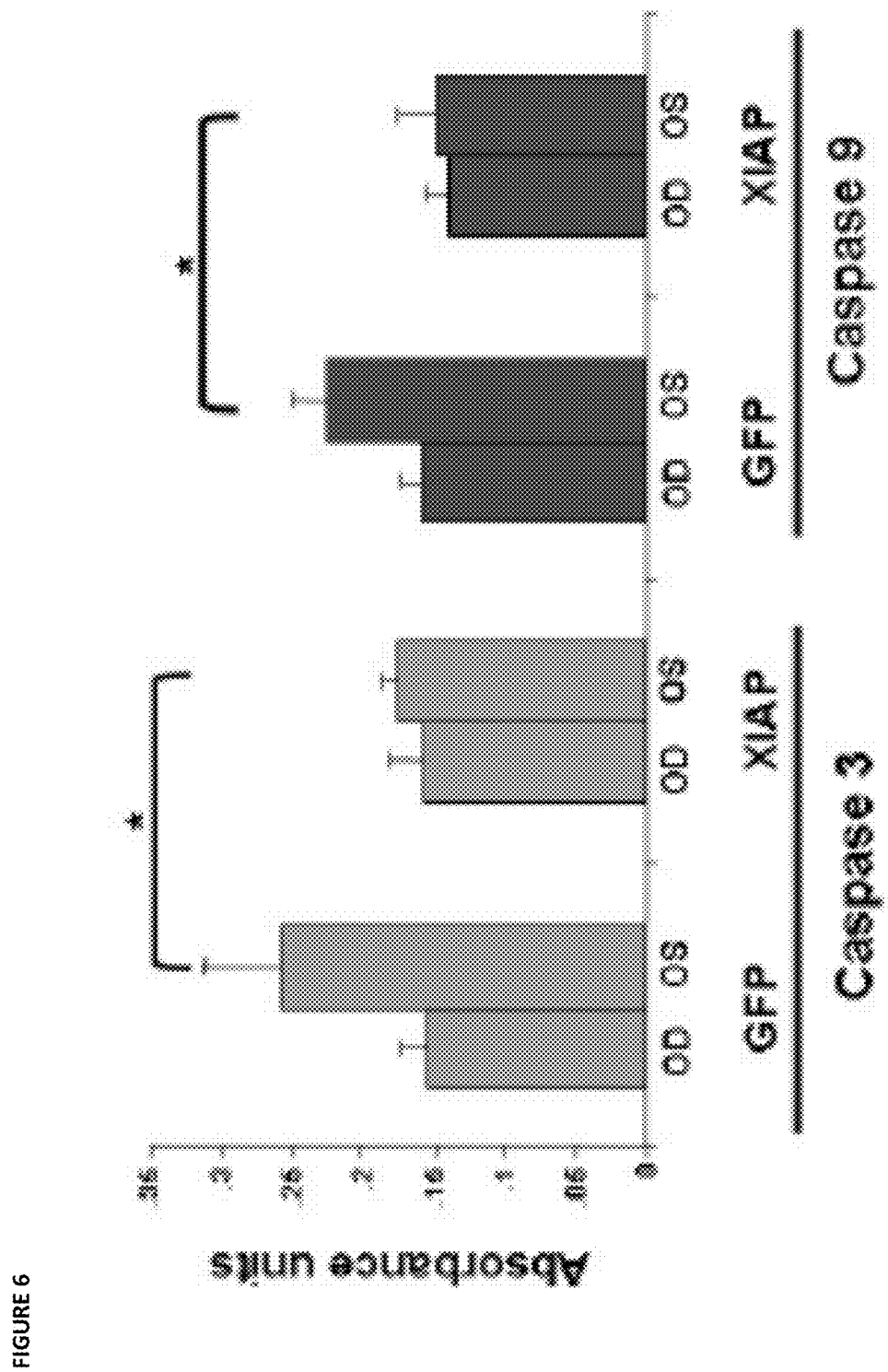
FIG. 6 shows Caspase 3 and 9 assays following retinal detachment in GFP and XIAP-treated retinas. Subretinal injections of rAAV-GFP or rAAV-XIAP were followed by retinal detachment in the left eye (OS) of the animal Right eyes (OD) served as intact controls.

Caspase Activity Assays rAAV-GFP served as a vector and surgical control, showing rates of photoreceptordegeneration. There was no evidence that rAAV-GFP had a neuroprotective effect or accelerated photoreceptor degeneration. Retinal detachment in the rAAV-GFP transfected eyes (GFPOS) showed the expected elevation in caspase 3 and 9 activity as compared to intact, nondetached retinas (SEE FIG. 6). Caspase activity levels in XIAP-treated retinas (XIAP-OS) showed no detachment-induced increase, and were comparable to their contralateral attached controls. All caspase activities were measured at 24 hours after the detachment, which was previously shown to be the time of peak caspase activity.

TUNEL Analysis

Figure 7:
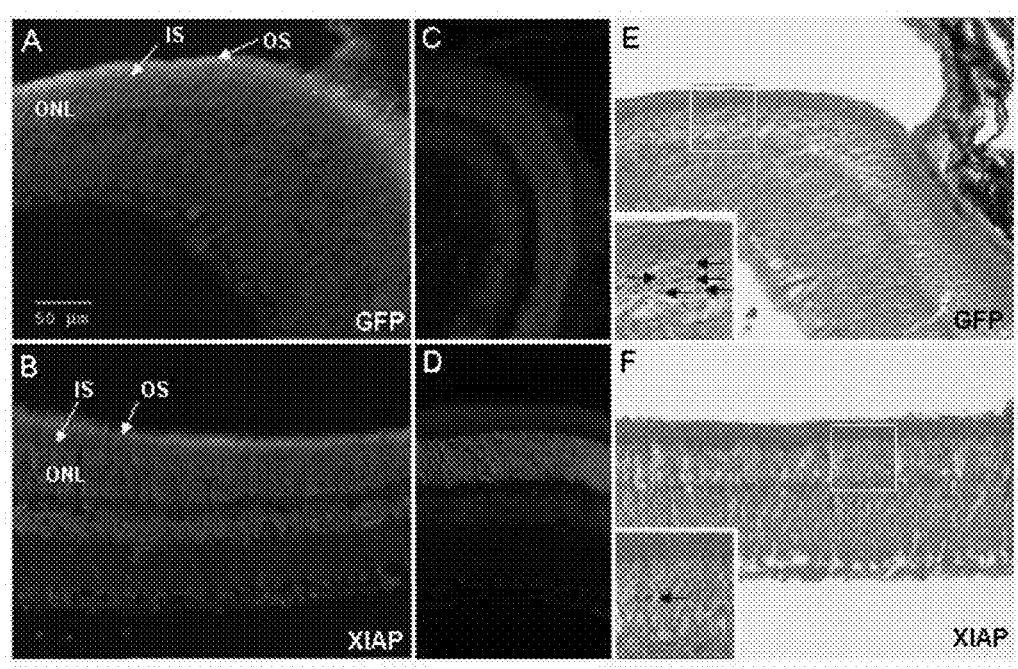
FIG. 7 shows Immunohistochemistry with antibodies to GFP (A) and to the HA tag of XIAP (B) confirmed robust over-expression in the cell bodies and inner (IS) and outer (OS) segments of the photoreceptors from both rAAV constructs. No primary antibody controls for GFP and XIAP are shown in C and D, respectively. TUNEL analysis confirmed that GFP-treated retinas had more apoptotic nuclei than XIAP-treated retinas (brown pigment in E, F and black arrows in insets). TUNEL-positive pixel counts (boxplot, G) supported the immunohistochemistry results. Each box contains the values between the 25th and 75th percentile, and the line within the box represents the median value. Bar lines above and below each box indicate the 90th and $10^{th}$ percentiles, respectively. The boxplot was generated with SigmaPlot, version 8.0 (SPSS, Inc.). ONL, outer nuclear layer.
Figure 7:
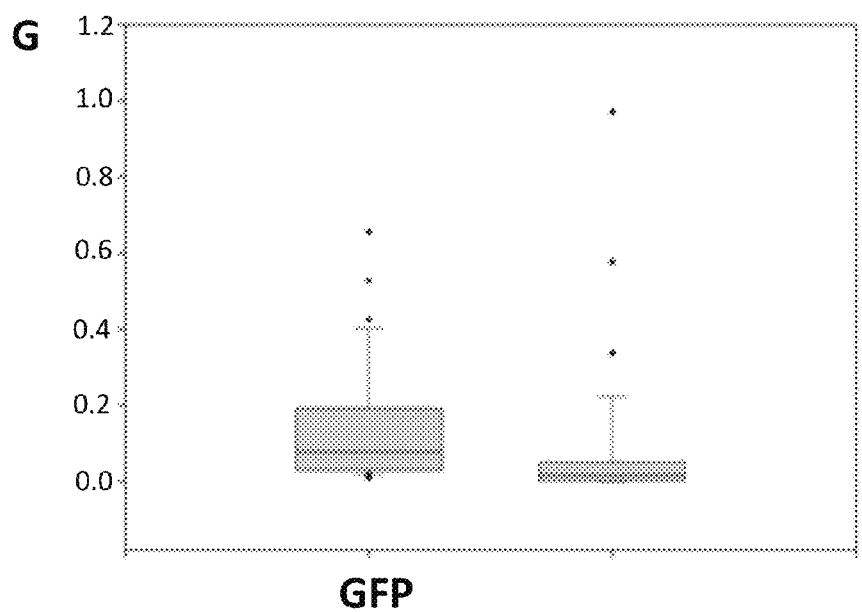

Eyes were sampled at 3 days following the creation of the retinal detachment, and were embedded, sectioned and processed for immunohistochemistry and TUNEL analysis. The 3 day time point was chosen because previous experimental studies in animal models demonstrated peak TUNEL-positive staining at 3 days after retinal detachment (Zacks et al. Invest Ophthalmol Vis Sci 2003; 44:1262-1267, Lewis G P, Charteris et al. Invest Ophthalmol Vis Sci 2002; 43:2412-2420, herein incorporated by reference in its entirety) Immunohistochemistry confirmed robust expression from both the rAAV-GFP and rAAV-XIAP viral injections (SEE FIG. 7A, B). Antibodies for GFP or XIAP identified strong staining in the cell bodies and inner and outer segments of the photoreceptors in the regions of the retinal detachments. This signal did not always cover the full detachment, and was sometimes found in attached portions of the retina, indicating that the viral transfections and the detachment did not always completely overlap. Automated, computer-based quantification of TUNEL staining showed that there were fewer TUNEL-positive cells in the rAAV-XIAP eyes than in the rAAV-GFP eyes (SEE FIG. 7C-E). Although the XIAP-related decrease in the number of TUNEL-positive cells did not reach statistical significance as compared to the GFP-treated eyes, the results do correlate well with XIAP-related decrease in caspase (SEE FIG. 6).

Photoreceptor Survival in Chronic Detachment

Figure 8:
FIG. 8 shows immunohistochemistry for GFP (A, B) and XIAP (D, E) confirmed sustained expression at 2 months after the detachment. The GFP signal (green) was faint because many of the photoreceptors expressing the viral transgene had died. In contrast, XIAP signal (red) was bright, and accompanied by increased numbers of photoreceptors. Note that in retinal areas where XIAP signal was reduced (arrowhead), photoreceptor loss was considerable. Rhodopsin staining (red) in GFP-injected (C) and XIAP-injected (F) retinas shows that the preserved photoreceptors are able to synthesize functional protein. Outer nuclear layer identified by arrow. Magnification bar=50 mm.
Figure 9:
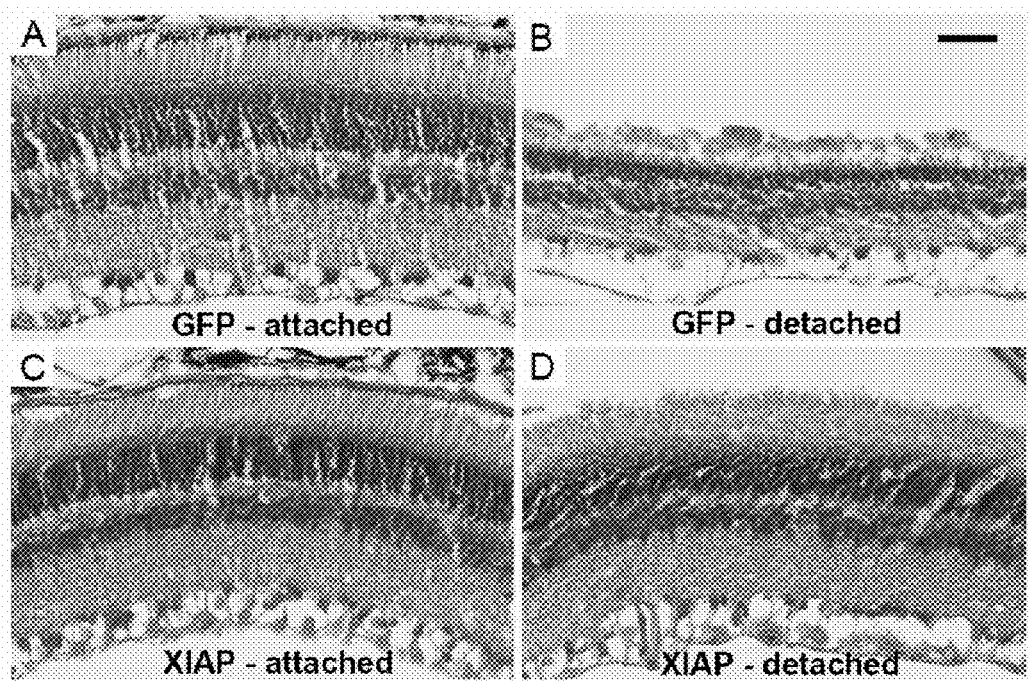
FIG. 9 shows Comparison between attached (A, C) and detached (B, D) retinas in XIAP and GFPtreated animals. At two months after detachment, XIAP-treated retinas (D) were consistently thicker than GFP-treated retinas (B) and their inner and outer segments were more organized. A ratio was obtained by dividing the number of nuclear layers in the ONL in a detached region of the eye by the number of nuclear layers in the ONL in the attached retina in the same eye (E). Magnification bar=50 mm.
Figure 9:
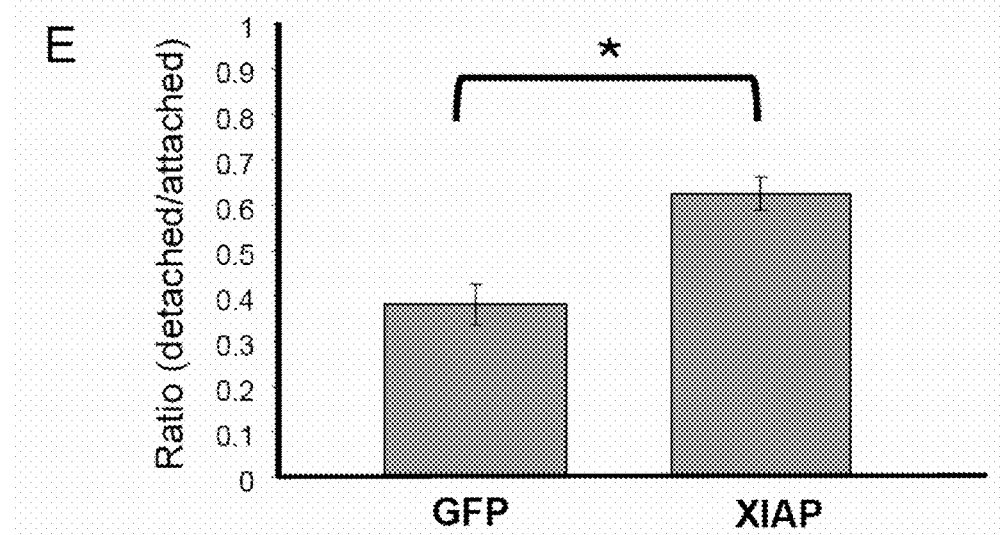

To assess long-term structural protection of photoreceptors, histology was conducted on eyes sampled at 2 months after the retinal detachment. Immunohistochemistry against GFP (SEE FIG. 8A, B) or XIAP (SEE FIG. 8D, E) was employed to visualize the site of rAAV virus injection and to correlate this with histological studies. Morphological differences were observed between XIAP-treated and GFP-treated retinas. The inner and outer segments of the XIAP-treated samples were generally more organized than those of the GFP-treated retinas, although less so than attached regions in the same eye. Rhodopsin staining confirmed that the preserved photoreceptors were viable and produced functional protein (SEE FIG. 8C, F). The layers of photoreceptor nuclei in the ONL were counted and compared between the detached retinas treated with either rAAV-XIAP or rAAV-GFP and their normal attached counterparts. Counts were always taken at the same distance from the optic nerve along the vertical meridian to account for the retinal thinning that naturally occurs as one moves towards the periphery of the eye. Overall, there was significant preservation of the ONL in the XIAP-treated detached retinas (SEE FIGS. 8 and 9). These retinas had from 4 to 8 nuclear layers (compared to 6 to 11 in the attached regions of the same eye). GFP-treated detached retinas had from 0 to 7 nuclear layers (with 6 to 14 in the attached portions of the same eyes). For each animal, a ratio of ONL nuclei in the detached relative to the attached regions was calculated (SEE FIG. 9E).

Example 5

MET Effects on Retinal Apoptosis

Figure 10:
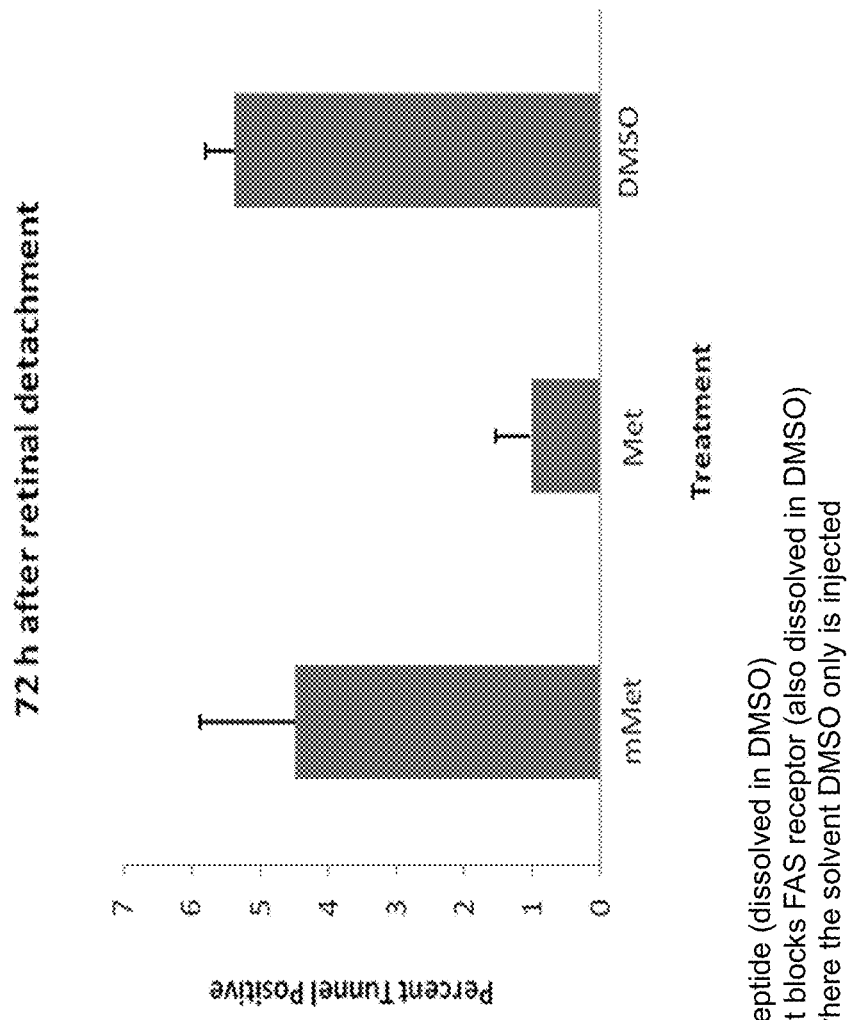
FIG. 10 shows a graph of the effects of MET on the number of TUNEL positive cells post retinal detachment.

In experiments performed during development of embodiments of the present invention, retinal detachments were created using standardized animal model (rat). At the time of retinal detachment, one of the three compounds was injected (mMET, MET, DMSO). At 72 hours post-detachment, the eyes harvested and processed for TUNEL staining. MET significantly reduced the number of TUNEL-positive cells (SEE FIG. 10) (i.e. reduced the number of apoptotic cells).

Figure 11:
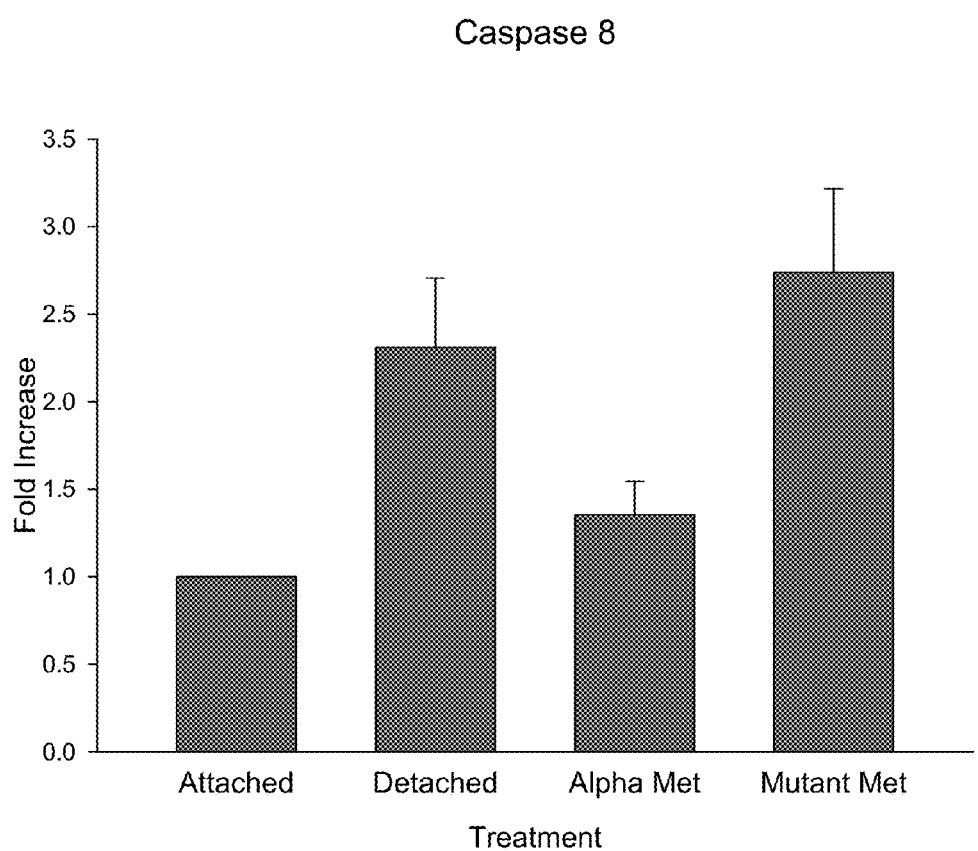
FIG. 11 shows a graph of the effect of MET on caspase activity induced by retinal detachment.

In experiments performed during development of embodiments of the present invention retinal detachments were created using a standardized animal model (rat). At 24 hours post-detachment, the eyes harvested and processed for caspase 8 activity assays. Caspase 8 is the first downstream target of FAS receptor activation. Increased caspase 8 activity means more FAS receptor activation. Alpha-Met (experimental compound) prevented the increase in caspase 8 activity caused by retinal detachment (SEE FIG. 11). Similar results were observed for two more caspases that are even farther downstream in the pathway, caspase 3 and 9.

Example 6

Compositions and Methods

Retinal-RPE separation was created in Brown Norway rats by subretinal injection of 1% hyaluronic acid. Met12, derived from the Fas-binding extracellular domain of the oncoprotein Met, was injected into the subretinal space at the time of separation. A mutant peptide or vehicle administered in a similar fashion acted as inactive controls. Extrinsic apoptotic pathway was induced in 661W cells using a Fas-activating antibody in the presence or absence of Met12. Caspase 3, caspase 8, and caspase 9 activities were measured with calorimetric and luminescent assays in retinal extracts and cell lysates. Terminal deoxynucleotidyl transferase dUTP nick-end labeling (TUNEL) was performed in retinal sections 3 days after separation. Histology was performed in retinal sections 2 months after retinal detachment.

Experimental Model of Retinal Detachment. Rodents were anesthetized with a 50:50 mix of ketamine (100 mg/mL) and xylazine (20 mg/mL), and pupils were dilated with topical phenylephrine (2.5%) and tropicamide (1%). A 20-gauge microvitreoretinal blade (Walcott Scientific, Marmora, N.J.) was used to create a sclerotomy 2 mm posterior to the limbus, carefully avoiding lens damage. Under direct visualization through an operating microscope, a Glaser subretinal injector (32-gauge tip; BD Ophthalmic Systems, Sarasota, Fla.) was introduced through the sclerotomy into the vitreous cavity and then through a peripheral retinotomy into the subretinal space. Sodium hyaluronate (10 mg/mL) (Pharmacia and Upjohn Co., Kalamazoo, Mich.) was slowly injected to detach the neurosensory retina from the underlying retinal pigment epithelium. In all experiments, approximately one-third to one-half of the supero-nasal neurosensory retina was detached. Detachments were created in the same location in all animals tested to allow for direct comparison of retinal cell counts. Detachments were created in the left eye, leaving the right eye as the control. In some eyes, a wild-type MetYLGA 12-mer (HHIYLGAVNYIY (SEQ ID NO:1), Met12, 50 μg), a mutant Met 12-mer (HHGSDHERNYIY (SEQ ID NO:2), mMet, 50 μg), or vehicle (DMSO) was injected into the subretinal space in the area of the detachment in a 10 μl volume using a Hamilton syringe (Hamilton Company, Reno, Nev.) immediately after the creation of the detachment.

Cell Culture. The 661W cell line was maintained in Dulbecco's modified Eagle's medium containing 10% fetal bovine serum, 300 mg/L glutamine, 32 mg/L putrescine, 40 μL/L of β-mercaptoethanol, and 40 μg/L of both hydrocortisone 21-hemisuccinate and progesterone. The media also contained penicillin (90 units/ml) and streptomycin (0.09 mg/ml). Cells were grown at 37° C. in a humidified atmosphere of 5% CO2 and 95% air.

Caspase Activity Assays. Caspase 3, caspase 8 and caspase 9 activities were measured with colorimetric tetrapeptide cleavage assay kits, per the manufacturer's instructions (Bio-Vision, Mountain View, Calif.). Total retinal protein was extracted as per a previously published protocol (Zacks et al. IOVS 2003; 44(3):1262-1267, herein incorporated by reference in its entirety). One hundred microgram of total retinal protein from either attached or detached retinas was incubated with caspase 3 (DEVD-pNA), caspase 8 (IETD-pNA) or caspase 9 substrates (LEHD-pNA) at 200 μM final concentration for 60 minutes. Absorbance was measured at 405 nm in a microplate reader (Spectra-MAX 190, Molecular Devices, Sunnyvale, Calif.). As a negative control, retinal protein was incubated with assay buffer without the tetrapeptide. A second negative control was used in which assay buffer alone was incubated with the tetrapeptide. As a positive control, purified caspase 3, caspase 8, or caspase 9 was incubated with the tetrapeptide alone. The caspase activity in the detached retina was normalized against the caspase activity in attached retina at the same time point. For each group, the data represents the average caspase activity levels of several (e.g. 5) independent samples, each sample consisting of protein from 5 eyes.

In cell culture experiments, caspase 8 activity was measured by a commercially available luminescent tetrapeptide (LETD) cleavage assay kit (Promega, Madison, Wis.). The 661W cells were seeded in 96-well plates (Nunc, Rochester, N.Y.) at 1500 cells/well for 24 hours prior to treatment. Cells were pre-treated with various concentrations of Met12, mMet, or vehicle for 1 hour prior to treatment with 500 ng/ml of Fas-agonistic Jo2 monoclonal antibody (BD Biosciences, San Jose, Calif.). Caspase 8 activity was measured at various time points by incubating the cells with the pro-luminescent substrate in 96-well plates following manufacturer's instructions. Controls included untreated cells and wells with no cells. Luminescence was measured in a plate reader luminometer (Turner Biosystems, Sunnyvale Calif.).

Western Blot Analysis. Retinas from experimental eyes with detachments and control eyes without detachments were dissected from the RPE-choroid, homogenized, and lysed in buffer containing 10 mM HEPES (pH 7.6), 0.5% IgEPal, 42 mM KCl, 1 mM phenylmethylsulfonyl fluoride (PMSF), 1 mM EDTA, 1 mM EGTA, 1 mM dithiothreitol (DTT), and 5 mM $MgCl_2$ and 1 tablet of protease inhibitors per 10 mL buffer (Complete Mini; Roche Diagnostics GmbH, Mannheim, Germany). The homogenates were incubated on ice and centrifuged at 22,000 g at 4° C. for 60 minutes. The protein concentration of the supernatant was then determined (DC Protein Assay kit; Bio-Rad Laboratories, Hercules Calif.). The protein samples were loaded and run on SDS-polyacrylamide gels (Tris-HCl Ready Gels; Bio-Rad Laboratories). After electrophoretic separation, the proteins were transferred onto polyvinylidene fluoride (PVDF) membranes (Immobilon-P; Amersham Pharmacia Biotech, Piscataway, N.J.). Protein bands were visualized with Ponceau S staining, and the lanes assessed for equal loading by densitometry of a nonspecific band present across all lanes. Membranes were then immunoblotted for cleaved caspase 3, cleaved caspase 8, and cleaved caspase 9 (Cell Signaling Technology, Danvers, Mass.) according to the manufacturer's instructions.

TUNEL Staining and Histology. At varying intervals after creation of the detachment, the animals were euthanized, and the eyes were enucleated. For TUNEL staining, whole eyes were fixed overnight at 4° C. in phosphate-buffered saline with 4% paraformaldehyde (pH 7.4). The specimens were embedded in paraffin and sectioned at a thickness of 5-6 μm. TUNEL staining was performed on the sections with the ApopTag Fluorescein In Situ Apoptosis Detection Kit according to the manufacturer's instructions (Millipore, Billerica, Mass.). For light microscopic analysis, paraffin sections were stained with 0.5% toluidine blue in 0.1% borate buffer.

Cell Counts and Retinal Thickness Measurements. Photoreceptor cell apoptosis was quantified as the percentage of total cells in the outer nuclear layer (ONL) that were TUNEL positive. Three non-overlapping high power fields (40×) at the maximal height of the retinal detachment were selected per section and were averaged unless there were less than three non-overlapping high power fields, in which case fewer fields were used. One representative section was used per eye. The total number of cells in the ONL was measured in a similar fashion. The total thickness of the retina (measured from the outer edge of the ONL to the inner limiting membrane) was measured in three places in each of three non-overlapping high power fields (40×) at the maximal height of the retinal detachment per section and averaged for each eye. Photoreceptor inner and outer segments were not included in the total retinal thickness measurement given variable retraction of these elements after detachment of the neurosensory retina which does not necessarily correlate with post-reattachment viability of the photoreceptors (Zou et al. Nat. Med. 2007 September; 13(9):1078-85, Guerin et al. Invest Ophthalmol Vis Sci. 1993; 34(1):175-183, herein incorporated by reference in their entireties). For toluidine blue stained specimens, normalization of ONL cell count to the total retinal thickness of each section (i.e., ONL cell count divided by total retinal thickness) was performed to account for possible differences in angles of sectioning and allow for inter-sample comparison. ONL cell counts and total retinal thicknesses in each group of the rat experiments were also normalized to corresponding values of attached retinas in that group to allow inter-sample comparison. For each experimental group, measurements were done on multiple sections (e.g., 3) from multiple eyes (e.g., 10), each eye from a separate animal.

Example 7

In Vitro Analysis of Met12

Figure 12:
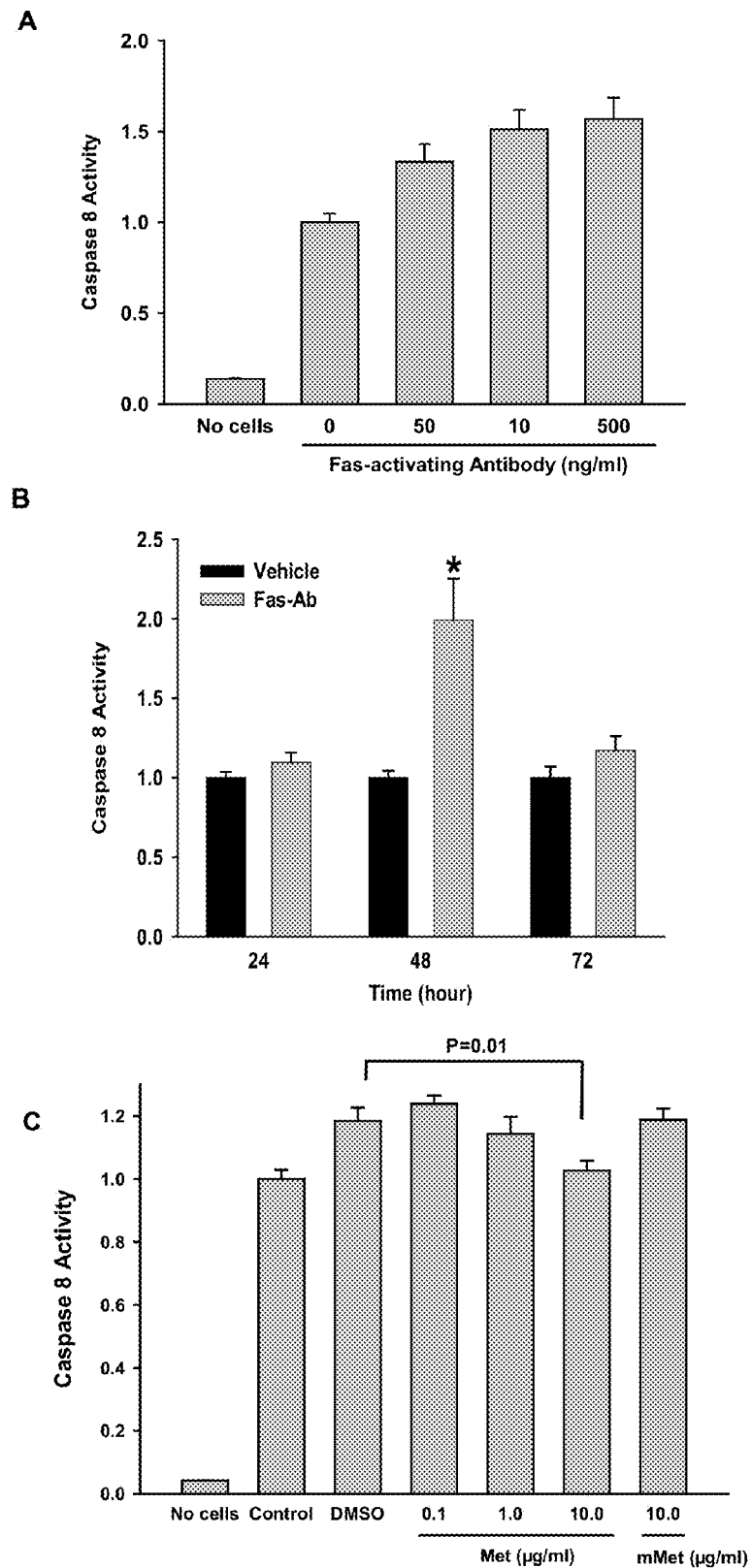
FIG. 12 shows Fas-induced caspase 8 activation is blocked by Met12 in 661W cells. A) 661W cells were treated with various concentrations of Fas-activating antibody (Fas-Ab). Caspase 8 activity was measured at 48 hours. Compared with no treatment, the increase in caspase 8 activity was statistically significant for all concentrations of Fas-Ab. B) 661W cells were treated with 500 ng/ml of Fas-Ab and caspase 8 activity was measured at various time points. Data was normalized to untreated controls at each time point. C) 661W cells were treated with 500 ng/ml Fas-Ab in the presence of Met12, mMet or vehicle (DMSO). Control group did not have Fas-Ab treatment. Caspase 8 activity was measured at 48 hours.

The 661W cell line is a photoreceptor line that has been immortalized by the expression of SV40-T antigen under control of the human interphotoreceptor retinol-binding protein (IRBP) promoter (Al-Ubaidi et al. J Cell Biol. 1992; 119(6):1681-1687, herein incorporated by reference in its entirety). 661W cells express cone photoreceptor markers, including blue and green cone pigments, transducin, and cone arrestin (Tan et al. Invest Ophthalmol Vis Sci. 2004; (3):764-768, herein incorporated by reference in its entirety), and can undergo caspase-mediated cell death (Kanan et al. Invest Ophthalmol Vis Sci. 2007; 48(1):40-51, herein incorporated by reference in its entirety). Previous experiments conducted during development of the present invention demonstrate that Fas signaling plays a critical role in caspase 8 activation and photoreceptor apoptosis in vivo. 661W cells were treated with a Fas-activating antibody (Fas-Ab). Addition of the Fas-Ab resulted in cell death. Activity of caspase 8 measured in 661W cell lysates increased with increasing concentration of Fas-Ab, peaking with the 500 ng/ml dose (SEE FIG. 12A). 661W cells were treated with 500 ng/ml Fas-Ab and measured activity levels at various time points. Caspase 8 activity was significantly increased at 48 hours in 661W cells exposed to Fas-Ab (SEE FIG. 12B).

Met inhibits the Fas pathway. A small 12-mer peptide, Met12, containing the amino acids surrounding the Fas-binding YLGA motif of Met protects Jurkat cells from FasL induced apoptosis (Zou et al. Nat Med. 2007 September; 13(9):1078-85, herein incorporated by reference in its entirety). 661W cells were treated with Fas-Ab in the presence of Met12 or the inactive mutant peptide, mMet, in which the central 6 amino acids containing the YLGA motif were randomly changed. Caspase 8 activity was determined 48 hours after treatment as a measure of Fas-receptor pathway activation. Fas-Ab induced caspase 8 activation was inhibited by Met12 treatment in a dose dependent manner (SEE FIG. 12C). In contrast, treatment of cells with the mMet peptide or vehicle alone had no effect on Fas-mediated caspase 8 activation. 661W cells have an intact Fas death receptor pathway. Met12 peptide can inhibit Fas signaling in an in vitro photoreceptor model.

Example 8

In Vivo Effect of Met12

Figure 13:
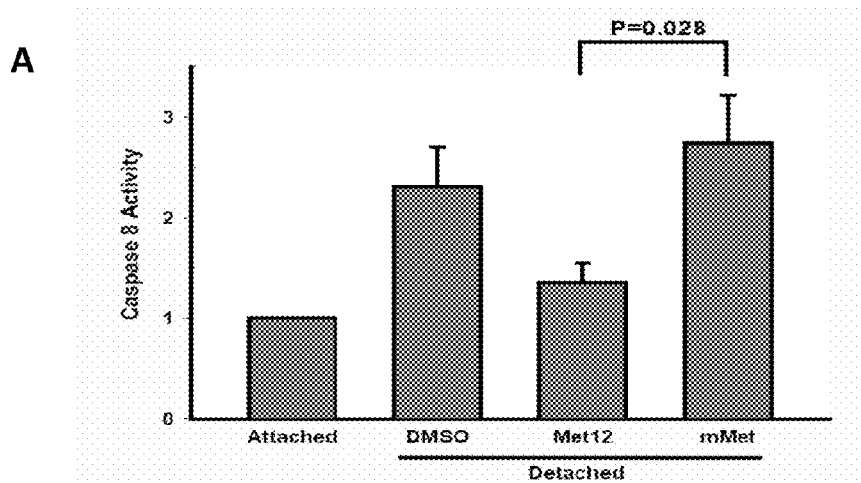
FIG. 13 shows Met12 inhibits activation of caspases. A) Injection of the Met12 into the subretinal space of detached retinas reduces caspase 8 activity. Rat retinas were detached in the presence of Met12 (50 µg), mMet (50 µg), or vehicle (DMSO). Caspase 8 activation was measured in harvested retinas after 24 hours of detachment as described. Data is presented as fold increase in caspase activity in detached retinas compared to attached retinas. Western blot shows decreased caspase 8 cleavage in the presence of Met12 (inset). Assay controls including no lysate samples (blank) and recombinant caspase 8 are shown. B) Caspase 3 activity was significantly reduced by Met12 treatment during retinal detachment. C) Caspase 9 activity was also significantly reduced by Met12. Data is presented as fold increase in caspase activity in detached retinas compared to attached retinas. Assay controls including no lysate samples (blank) and recombinant caspase 8 or caspase 9 are shown.
Figure 13:
Figure 13:
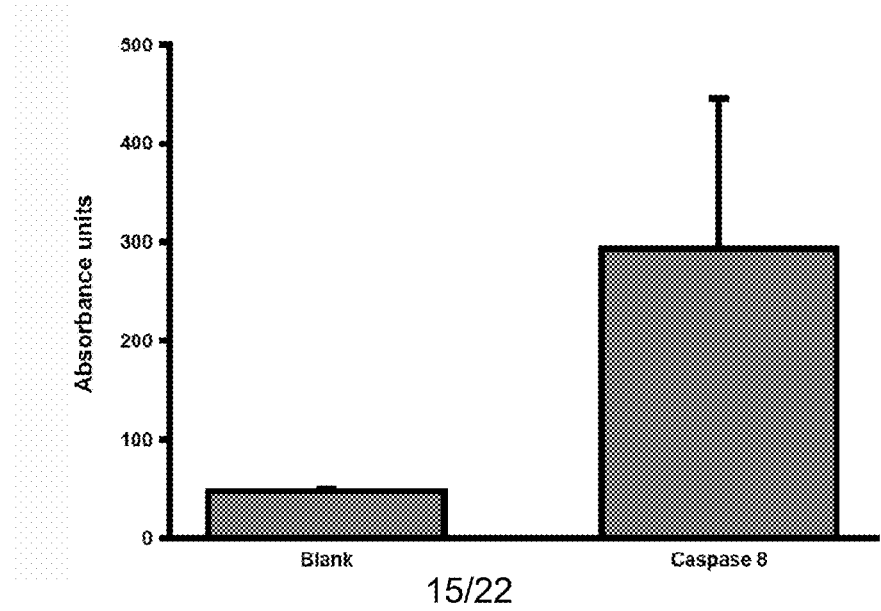
Figure 13:
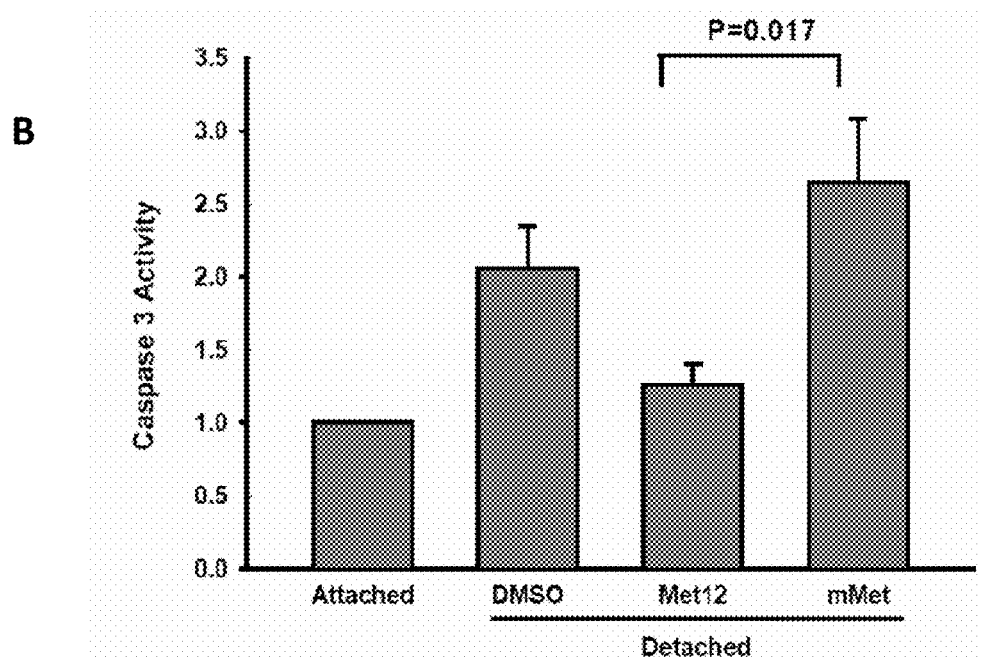
Figure 13:
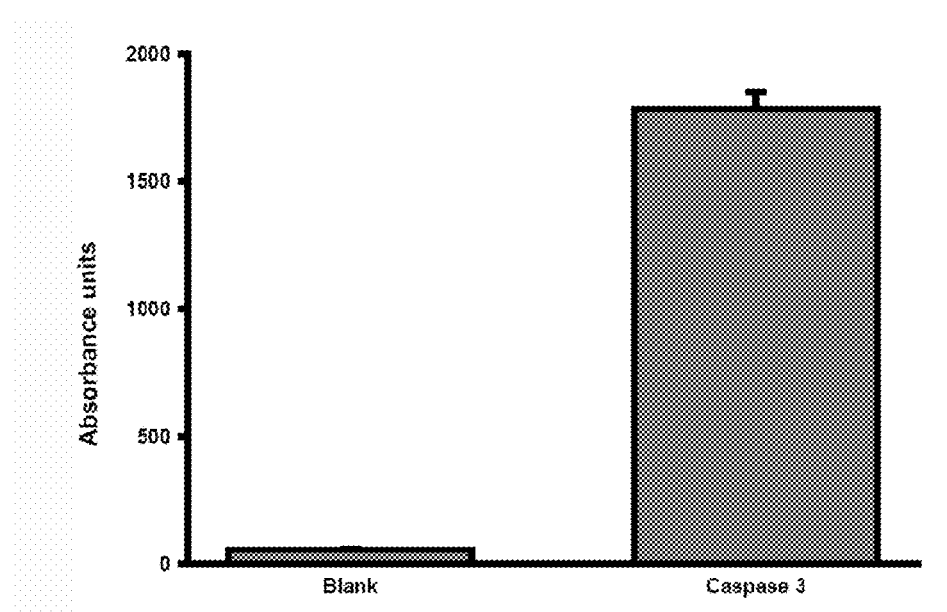
Figure 13:
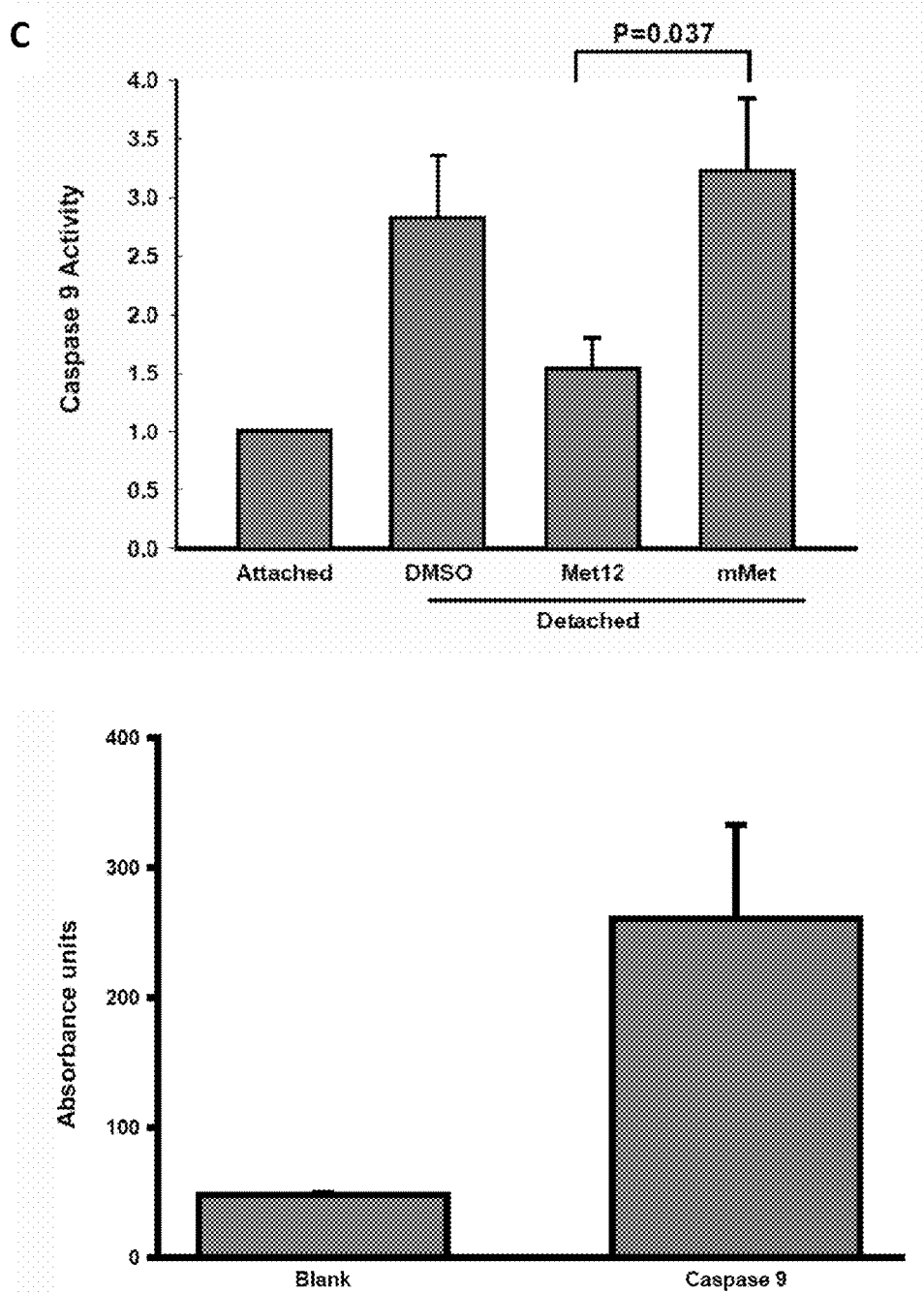

Experiments conducted during development of the present invention demonstrated that retinal detachment leads to the activation of Fas/FasL pathway and caspase 8 cleavage (Zacks et al. IOVS 2003; 44(3):1262-1267, Zacks et al. Arch Ophthalmol 2007; 125:1389-1395, Zacks et al. IOVS 2004; 45(12):4563-4569.8, herein incorporated by reference in their entireties). The effect of Met12 on photoreceptor caspase 8 activation 24 hours after retinal detachment was examined Rat retinas were detached in the presence of Met12 (50 μg), mMet (50 μg), or vehicle. Caspase 8 activity was significantly increased in detached retinas injected with vehicle or mMet, compared to attached retinas (SEE FIG. 13). Subretinal injection of the Met12 peptide at the time of retinal detachment reduced caspase 8 activity by approximately 50%. These results demonstrated that similar to 661W cells, treatment of detached retinas with Met12 inhibits Fas-mediated caspase 8 activation in photoreceptors.

During rodent photoreceptor apoptosis, Fas/FasL signaling acts as an upstream regulator of the intrinsic death pathway. This is demonstrated by the reduction of caspase-9 activity after injection of neutralizing antibodies against either Fas or FasL into the subretinal space of the detached retina (Zacks et al. IOVS 2004; 45(12):4563-4569.8, herein incorporated by reference in its entirety). Caspase 3 and caspase 9 activity levels were measured 24 hours after retinal detachment in the presence of Met12 (50 μg), mMet (50 μg), or vehicle. Subretinal Met12 injection reduced caspase 3 activity by approximately 50% after 24 hours (SEE FIG. 13). Similarly, caspase 9 activity was also reduced by about 50% in detached retinas injected with Met12 (SEE FIG. 13). In contrast, subretinal injection of the mMet did not affect the activity level of either of these caspases. The conversion of pro-caspase 8 to cleaved caspase 8 was confirmed on Western blot (SEE FIG. 13), as was the cleavage of caspases 3 and 9. These results demonstrated that Met12-mediated inhibition of the Fas-receptor leads to reduced activation of the intrinsic cell death pathway in detached photoreceptors.

Figure 14A:
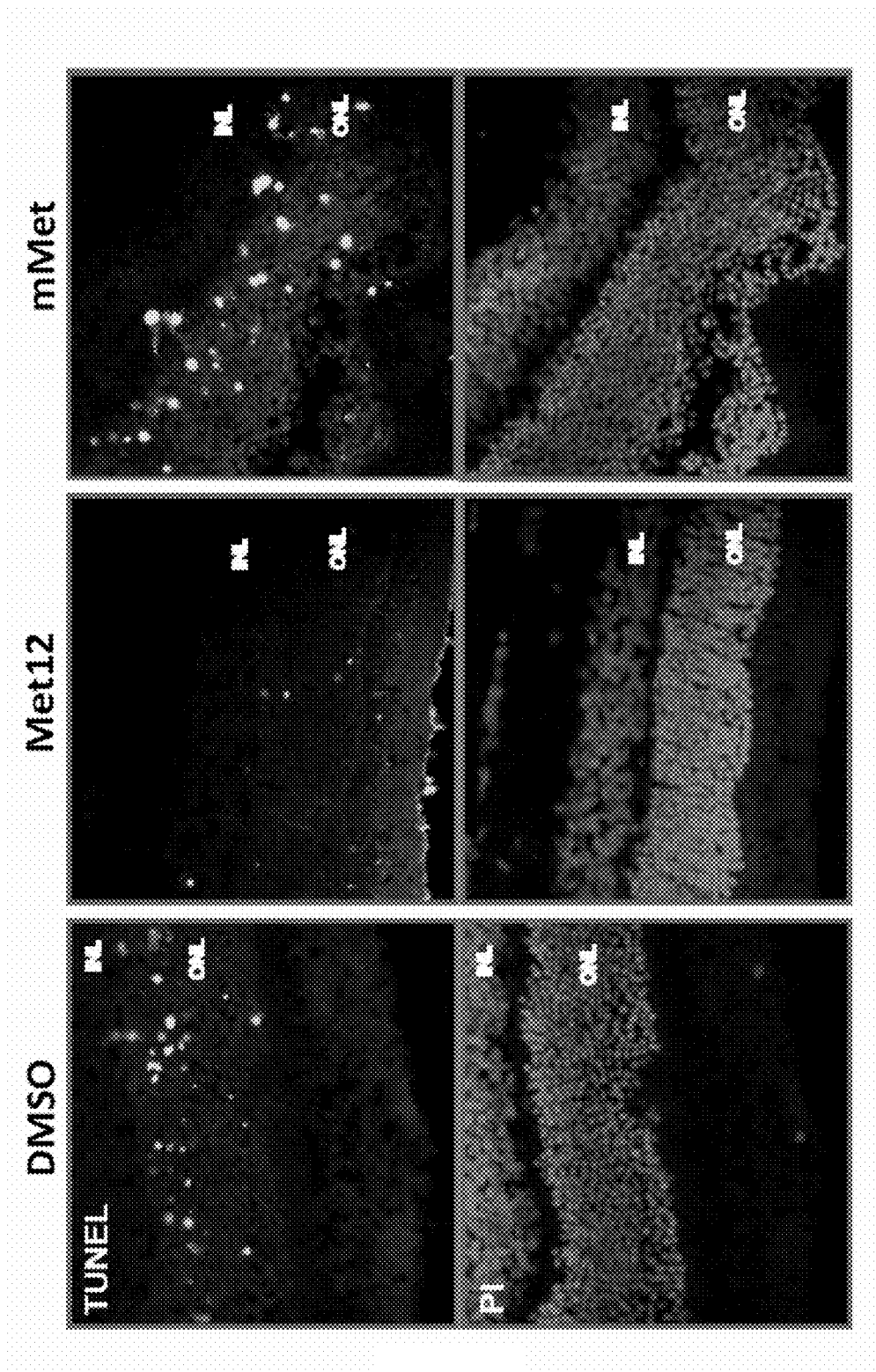
FIG. 14 shows Met12-mediated inhibition of Fas-pathway signaling prevents photoreceptors from entering the apoptotic cascade. Rat retinas were detached in the presence of Met12 (50 µg), mMet (50 µg), or vehicle (DMSO). Eyes were enucleated after 72 hours and retinas were sectioned for TUNEL staining. A) Representative photomicrographs of TUNEL stained photoreceptors after 72 hours of retinal detachment. Nuclei of retinal cells are stained with propidium iodide (PI). INL: Inner nuclear layer, ONL: Outer nuclear layer. B) Quantification of TUNEL positive cells in the ONL, mean±S.E., n=3-6. There was no TUNEL stained cells in the ONL of attached retinas.
Figure 14B:
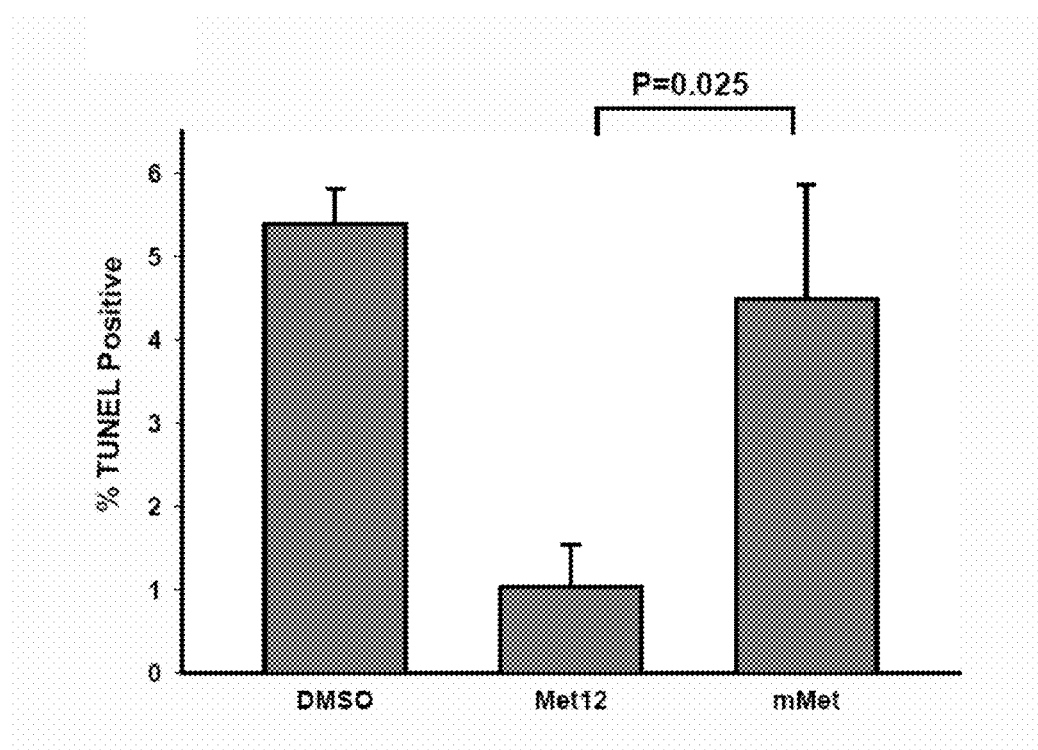

In rodent eyes, the peak of TUNEL staining occurs at 3 days after retina/RPE separation, with a rapid decline in TUNEL-positive cells to near pre-separation levels by day 7 (Zacks et al. IOVS 2003; 44(3):1262-1267, Zacks et al. Arch Ophthalmol 2007; 125:1389-1395, herein incorporated by reference in their entireties). Rat retinas were detached in the presence of Met12, mMet, or vehicle. At 3 days after retinal detachment, TUNEL positive cells were confined to the ONL of photoreceptors (SEE FIG. 14A). About 5% of ONL cells displayed TUNEL-positive staining at day 3 post-separation (SEE FIG. 14B). Injection of Met12 into the subretinal space resulted in ~77% fewer TUNEL-positive photoreceptors as compared with separated retinas injected with mMet (SEE FIG. 14B). No gross histological change could be detected due to injection of the vehicle alone.

Figure 15:
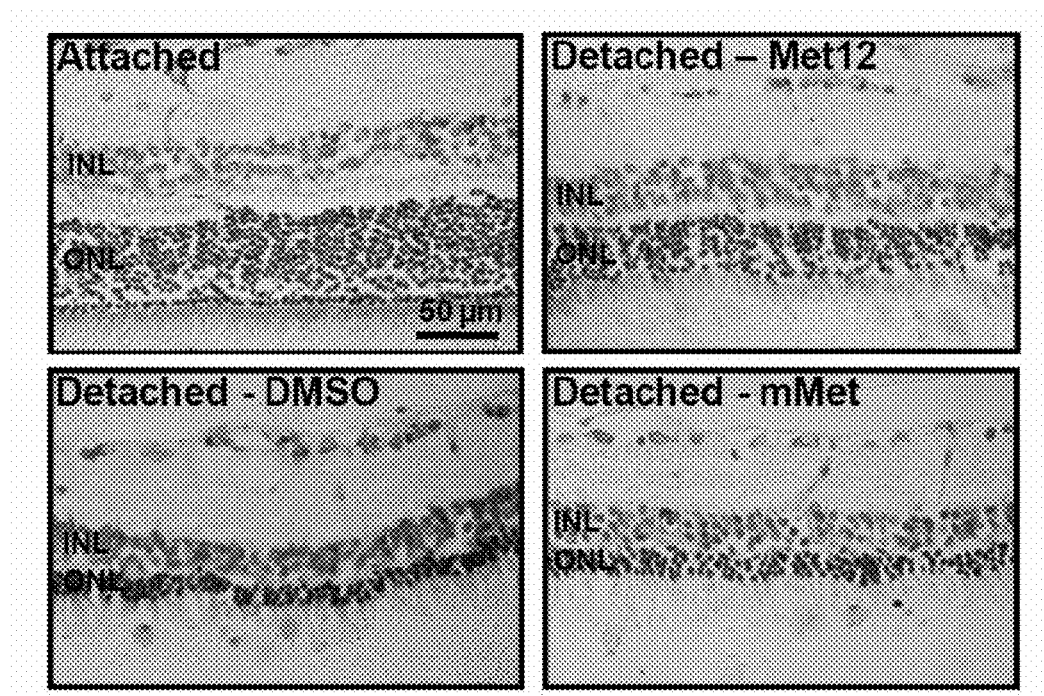
FIG. 15 shows decrease in caspase activation and the number TUNEL-positive cells correspond to increased long-term survival of photoreceptors. Retinas were detached in the presence of Met12 (50 µg), mMet (50 µg), or vehicle (DMSO), which were injected in the subretinal space at the time of detachment. Eyes were enucleated after 2 months of detachment and paraffin sections were stained with 0.5% toluidine blue. A) Representative photomicrographs, INL: Inner nuclear layer, ONL: Outer nuclear layer, B) ONL cell counts normalized to retinal thickness, C) ONL thickness normalized to retinal thickness.
Figure 15:
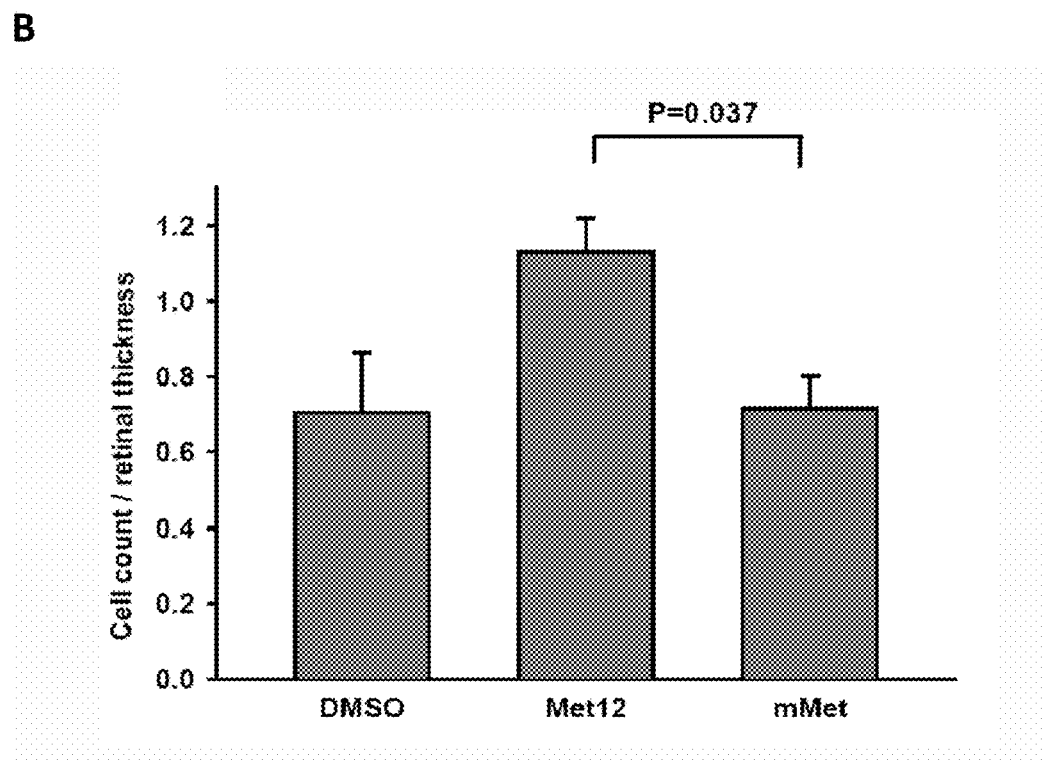
Figure 15:
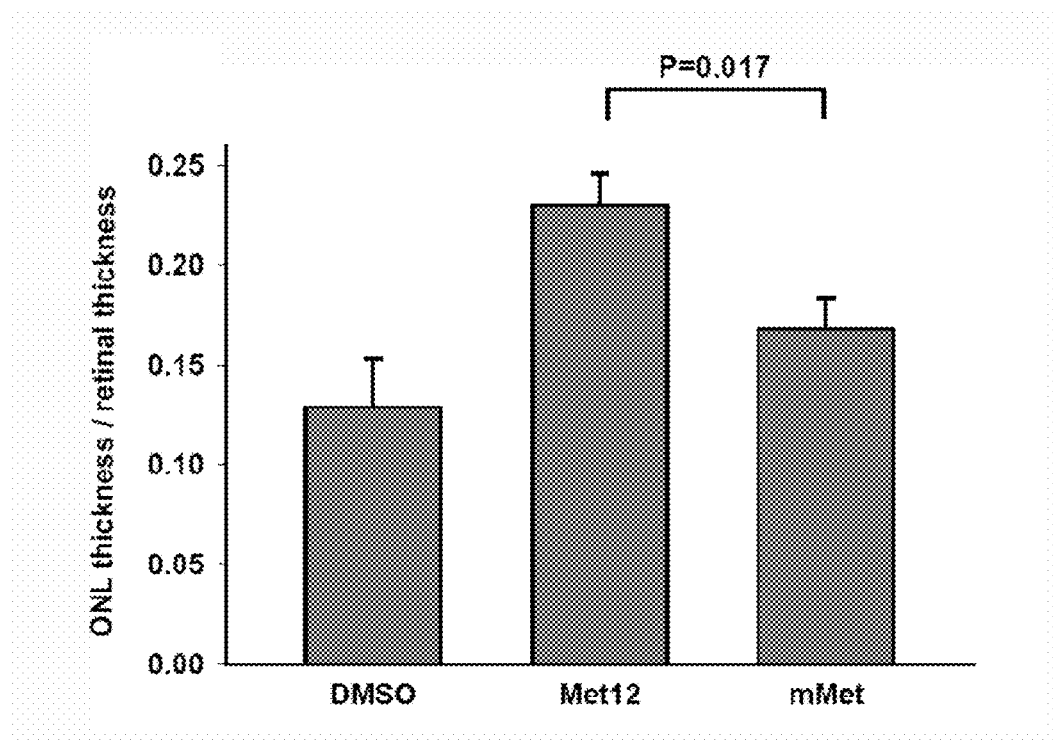

Rat retinas were detached as described above and Met12, mMet, or vehicle was injected in the subretinal space at the time of detachment. After 2 months, detached retinas showed significant reduction in ONL thickness as compared with attached retinas (SEE FIG. 15A). Rat retinas injected with Met12 showed 37% increase in ONL cell counts (SEE FIG. 15B) and 27% increase in ONL thickness measurements (SEE FIG. 15C) compared with mMet-injected retinas after 2 months of retinal detachment. These results demonstrated that inhibition of Fas signaling and caspase activation by Met12 increases the survival of photoreceptors after prolonged retina/RPE separation.

I claim:

1. A method of inhibiting photoreceptor apoptosis comprising administering to a subject a photoreceptor protective composition comprising a photoreceptor protective polypeptide comprising: a) a fragment of MET comprising SEQ ID NO:1(MET12), or (b) a fragment of MET that comprises at least 70% sequence similarity to MET12, wherein said polypeptide inhibits FAS-mediated photoreceptor apoptosis, and wherein said photoreceptor protective composition is administered to said subject intraocularly, intravitrealy, or periocularly.

2. A method of inhibiting photoreceptor apoptosis comprising administering to a subject a photoreceptor protective composition comprising a photoreceptor protective polypeptide comprising: a) a fragment of MET comprising SEQ ID NO:1(MET12), or (b) a fragment of MET that comprises at least 70% sequence similarity to MET12, wherein said polypeptide inhibits FAS-mediated photoreceptor apoptosis, and wherein said subject suffers from an ocular condition, disease, or condition or disease affecting ocular health.

3. The method of claim 2, wherein said subject suffers from abnormal retina-RPE (retinal pigment epithelium) homeostasis.

4. The method of claim 3, wherein said photoreceptor protective composition inhibits photoreceptor apoptosis until normal retina-RPE homeostasis is restored.

5. The method of claim 2, wherein said ocular condition, disease, or condition or disease affecting ocular health comprises retinal detachment, macular degeneration, retinitis pigmentosa, ocular inflammation, autoimmune retinopathy, trauma, cancer, tumor, uveitis, hereditary retinal degeneration, diabetic retinopathy, choroidal neovascularization, retinal ischemia, pathologic myopia, angioid streaks, macular edema, or central serous chorioretinopathy.

6. The method of claim 5, wherein said ocular condition, disease, or condition or disease affecting ocular health comprises macular degeneration.

7. The method of claim 5, wherein said photoreceptor protective composition is administered in an amount sufficient to enhance photoreceptor survival within said subject.

* * * * *

SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

His His Ile Tyr Leu Gly Ala Val Asn Tyr Ile Tyr
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

His His Gly Ser Asp His Glu Arg Asn Tyr Ile Tyr
1               5                   10